(12) United States Patent
Heydlauf

(10) Patent No.: US 9,398,265 B2
(45) Date of Patent: *Jul. 19, 2016

(54) METHOD AND APPARATUS FOR REMOTE MULTIPLE-PROCESS GRAPHICAL MONITORING

(71) Applicant: Siemens Healthcare Diagnostics Inc., Tarrytown, NY (US)

(72) Inventor: Michael W. Heydlauf, Raleigh, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 101 days.

This patent is subject to a terminal disclaimer.

(21) Appl. No.: 14/174,974

(22) Filed: Feb. 7, 2014

(65) Prior Publication Data

US 2014/0152820 A1    Jun. 5, 2014

Related U.S. Application Data

(63) Continuation of application No. 12/810,035, filed as application No. PCT/US2008/085222 on Dec. 2, 2008, now Pat. No. 8,648,910.

(60) Provisional application No. 61/016,966, filed on Dec. 27, 2007.

(51) Int. Cl.
   *H04N 7/18*   (2006.01)
   *H04N 5/33*   (2006.01)
   (Continued)

(52) U.S. Cl.
   CPC ........... *H04N 7/18* (2013.01); *G01N 33/54366* (2013.01); *G01N 35/00871* (2013.01); *G01N 2035/00891* (2013.01)

(58) Field of Classification Search
   CPC ...... H04L 51/043; H04L 51/046; H04N 7/15; H04N 7/18; H04N 2201/0013; H04N 2201/0089; H04N 2201/3273; H04N 1/00129; H04N 1/2125; G01N 35/00871; G01N 35/54366
   USPC ............ 348/52, 135, 143, 164; 709/203, 218, 709/224, 231, 248
   See application file for complete search history.

(56) References Cited

U.S. PATENT DOCUMENTS 6,404,906 B2   6/2002   Bacus et al.
6,871,324 B2 *  3/2005   Hand ................... H04L 41/046
                                                        709/223

(Continued)

FOREIGN PATENT DOCUMENTS

| CN | 101042300 | 9/2007 |
|----|-----------|--------|
| JP | 2003111017 | 9/2001 |

(Continued)

OTHER PUBLICATIONS

International Search Report for application No. PCT/US2008/085222 dated Feb. 9, 2009.

*Primary Examiner* — Farzana Huq

(57) ABSTRACT

A network of controllers for controlling and monitoring associated assay testing systems coupled to a remote monitoring unit for monitoring and controlling the controllers and/or the assay testing systems is disclosed. Each controller transmits a display image representing the status of the respective assay testing system. The remote monitoring unit automatically detects if the number of display images from the controllers is greater than a threshold number of displayable, static thumbnail images and, when the threshold is exceeded, displays thumbnail images dynamically in a scrolling or streaming motion. The thumbnail images, whether static or dynamic, are updated in real-time or pseudo-real-time to reflect updated status of the assay testing systems.

18 Claims, 16 Drawing Sheets

(51) Int. Cl.
   *G06F 15/16*    (2006.01)
   *G01N 33/543*   (2006.01)
   *G01N 35/00*    (2006.01)

(56) References Cited

U.S. PATENT DOCUMENTS

| | | | |
|---|---|---|---|
| 6,901,442 B1 * | 5/2005 | Schwaller | H04L 43/0817 709/223 |
| 7,667,719 B2 | 2/2010 | Goodwin et al. | |
| 8,069,239 B2 * | 11/2011 | Trochman | G08C 19/00 348/135 |
| 2001/0034068 A1 | 10/2001 | Spivey et al. | |
| 2004/0058432 A1 | 3/2004 | Owen et al. | |
| 2004/0162898 A1 | 8/2004 | Rich | |
| 2004/0246270 A1 | 12/2004 | Krishnamurthy et al. | |
| 2005/0074362 A1 | 4/2005 | Lappe et al. | |
| 2005/0137653 A1 | 6/2005 | Friedman et al. | |
| 2007/0282997 A1 | 12/2007 | Trochman | |
| 2008/0034325 A1 * | 2/2008 | Ording | G06F 3/04817 715/838 |
| 2008/0273110 A1 | 11/2008 | Joza et al. | |
| 2009/0268075 A1 | 10/2009 | Yumiki | |

FOREIGN PATENT DOCUMENTS

| | | |
|---|---|---|
| JP | 2005106746 | 10/2003 |
| JP | 2006270666 | 3/2005 |
| WO | 2007086140 | 2/2007 |

* cited by examiner

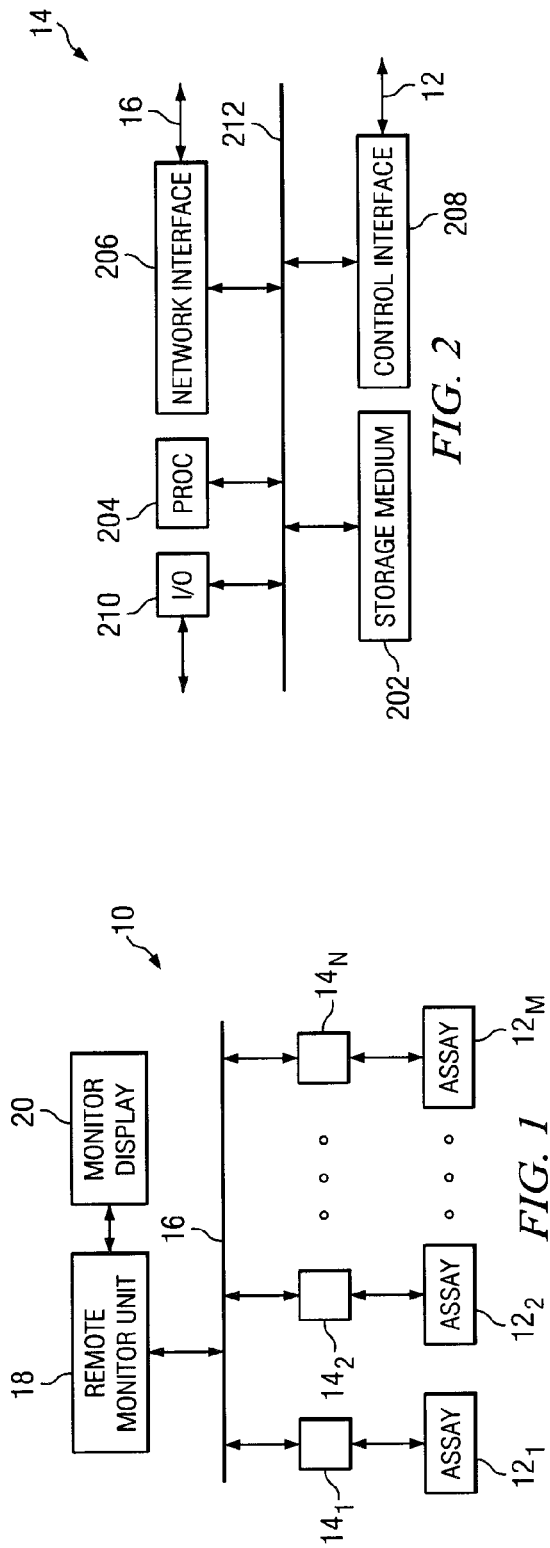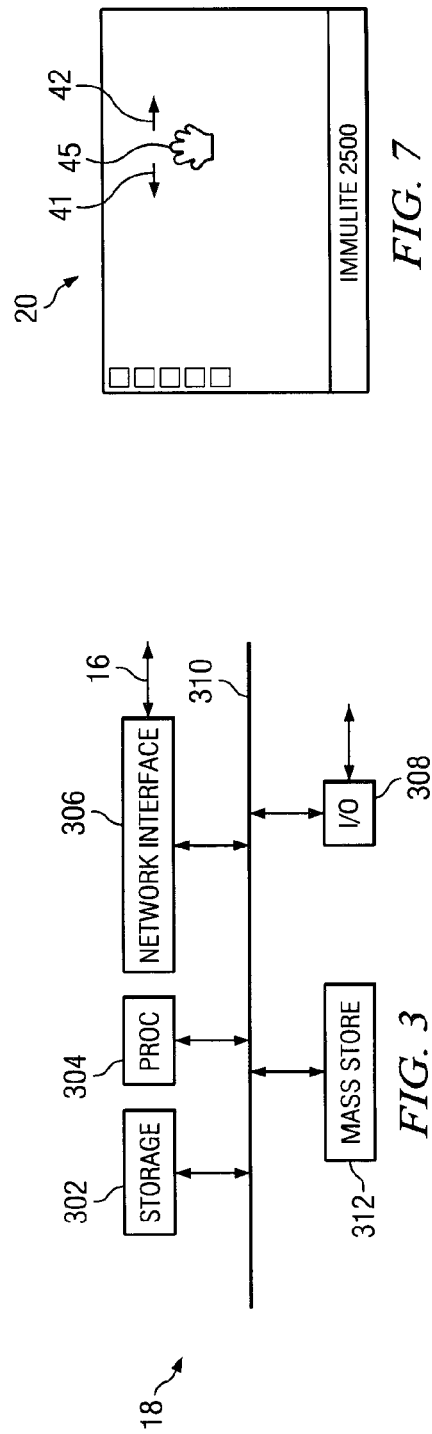

FIG. 11

METHOD AND APPARATUS FOR REMOTE MULTIPLE-PROCESS GRAPHICAL MONITORING

CROSS REFERENCE TO RELATED APPLICATIONS

This is a continuation application claiming priority from U.S. Ser. No. 12/810,035 filed Jun. 22, 2010 which is a National Stage of PCT/US2008/085222 filed Dec. 2, 2008 which claims priority from U.S. Provisional Ser. No. 61/016,966 filed Dec. 27, 2007 which is hereby incorporated by reference herein.

TECHNICAL FIELD

The field of the invention is related to remote monitoring and, more specifically, to real-time or pseudo-real-time remote monitoring that includes remote video display of a plurality of processes.

BACKGROUND OF THE INVENTION

Conventional assay systems include multiple testing stations, a plurality of vessels for holding samples, a conveyor means for moving the vessels in various sequences from testing station to testing station, and a controller for controlling the sequence(s) of tests on the vessel contents in accordance with established protocols. Typically, the controller is disposed local to the assay testing system.

For various purposes, including efficiency, safety, and quality, the controllers of plural assay systems may be connected to a remote monitoring unit through a local area network, wide area network or other communication means. The remote monitoring unit typically includes a controller, a display device(s) having a video monitor screen(s), and a graphical user interface (GUI).

The video monitor screen of the display device at the remote monitoring unit, or "remote monitor screen", provides graphical images of the operating status of the remotely monitored assay system. Generally, the graphical image(s) shown on the remote monitor screen replicate the image(s) shown on the monitor screen of the local controller.

Problems arise from such a system, however, especially when multiple assay systems having multiple testing stations are monitored by a single remote monitoring unit. For example, graphical images from each of the multiple monitored assay processes must be communicated to the remote monitor screen concurrently. Moreover, the communicated image(s) of each assay process that is/are displayed on the remote monitor screen must be sufficiently large, to be visible, and provide sufficient detail, to make the image(s) understandable to the remote user. Furthermore, the number of automated processes that must be concurrently visible on the remote monitor screen varies with time and with the number of assay systems.

However, the remote monitor screen of the display device at the remote monitoring unit has a given, fixed viewing area. Although larger screen areas are one solution to the problem, large screens are more expensive and a single large screen does not provide redundancy in the event of a malfunction. Therefore, a system and method for displaying, in real-time or in pseudo-real-time, the status of a variable number of processes concurrently being executed on a multiplicity of monitored assay testing systems, on a single, remote monitor screen is needed. Moreover, a system and method for automatically and dynamically allocating predetermined portions of the remote monitor screen to display and continuously update images of the monitored assay systems in real-time or pseudo-real-time is needed, whereby that information associated with some or all of the remote processes and some or all of the multiplicity of assay systems is provided to the user graphically.

BRIEF SUMMARY OF THE INVENTION

Automated, multiple-process assay systems, for testing and transporting vessels containing samples of, for example, a biological fluid or other material are disclosed. The systems include plural testing stations for performing various tests on the samples according to pre-established protocols, and plural conveyor mechanisms for transporting the vessels through various sequences, from one testing station to another testing station.

The automated, multiple-process assay systems can be disposed in a room(s) or other physical area of a laboratory (hereinafter a "zone"). The number of assay systems and the number of testing stations associated with each assay system for each zone will be predetermined. However, the number of assay systems, the number of testing stations associated with each assay system, and/or the number of vessels undergoing a process at a discrete testing station can change with time.

Each of the monitored assay systems further includes an associated controller that is generally, but not necessarily, located proximate to the associated monitored assay system.

The system includes at least one remote monitoring unit having a processor and a monitor display screen, for visually monitoring graphical images transmitted by the controllers associated with each of the monitored assay systems. The remote monitoring unit is in communication with the controllers via a communication network. The remote monitoring unit is adapted for a single user to monitor and control the plural controllers remotely.

Controllers are arranged to communicate local controller display images to the remote monitoring unit. Local controller display images graphically represent data, parameters, and status and inventory information concerning the operation of the respective monitored assay system. The remote monitoring unit's processor automatically and continuously determines the number of local controller display images being received and, if the number of received local controller display images is below a predetermined display threshold, all of the local controller display images are displayed on the monitor display screen concurrently as thumbnail images. If the number of local controller display images is greater than the predetermined display threshold, local controller display images are displayed as a sliding window of dynamic, thumbnail images, for example, by ticker-tape scrolling or streaming motion.

For example, if processes on eight assay systems are being monitored remotely at a remote monitoring unit and the predetermined display threshold is only four, then dynamic, scrolling or streaming thumbnail images of all or some portion of four or five of the processes will be visible as a moving horizontal bar of dynamic images at any given instant. The speed or rate of advance of the scrolling or streaming motion can be pre-set or selectively adjusted so that each dynamic image is visible on the remote monitor screen for a sufficient period of time so that any issues relating to the controller and/or the monitored assay system associated with a respective dynamic image will be displayed and visible for a desired period of time. The scrolling and streaming motion of the dynamic images thus enables the remote user to visually monitor more processor displays remotely than could be effectively monitored on a conventional system.

Advantageously, the static and dynamic images are continuously updated to provide real-time and/or pseudo-real time status of each of the monitored assay systems.

BRIEF DESCRIPTION OF THE SEVERAL VIEWS OF THE DRAWINGS

The invention will be more fully understood by reference to the following Detailed Description of the invention in conjunction with the Drawing, of which:

FIG. 1 shows a block diagram of a system for remotely monitoring and controlling a plurality of assay systems in accordance with the present invention;

FIG. 2 shows a block diagram of a controller for controlling a monitored assay system in accordance with the present invention;

FIG. 3 shows a block diagram of a remote monitoring unit for remotely monitoring and controlling the controllers and assay systems in accordance with the present invention;

FIG. 7 shows an illustrative example of a screen image having a "grab-hold" icon;

FIG. 11 shows an illustrative example of a screen image having a general flag summary window;

FIG. 12B shows the illustrative example of the screen image of

FIG. 12A further having a window for configuring instruments and inventory flags;

DETAILED DESCRIPTION OF THE INVENTION

Figure 4:
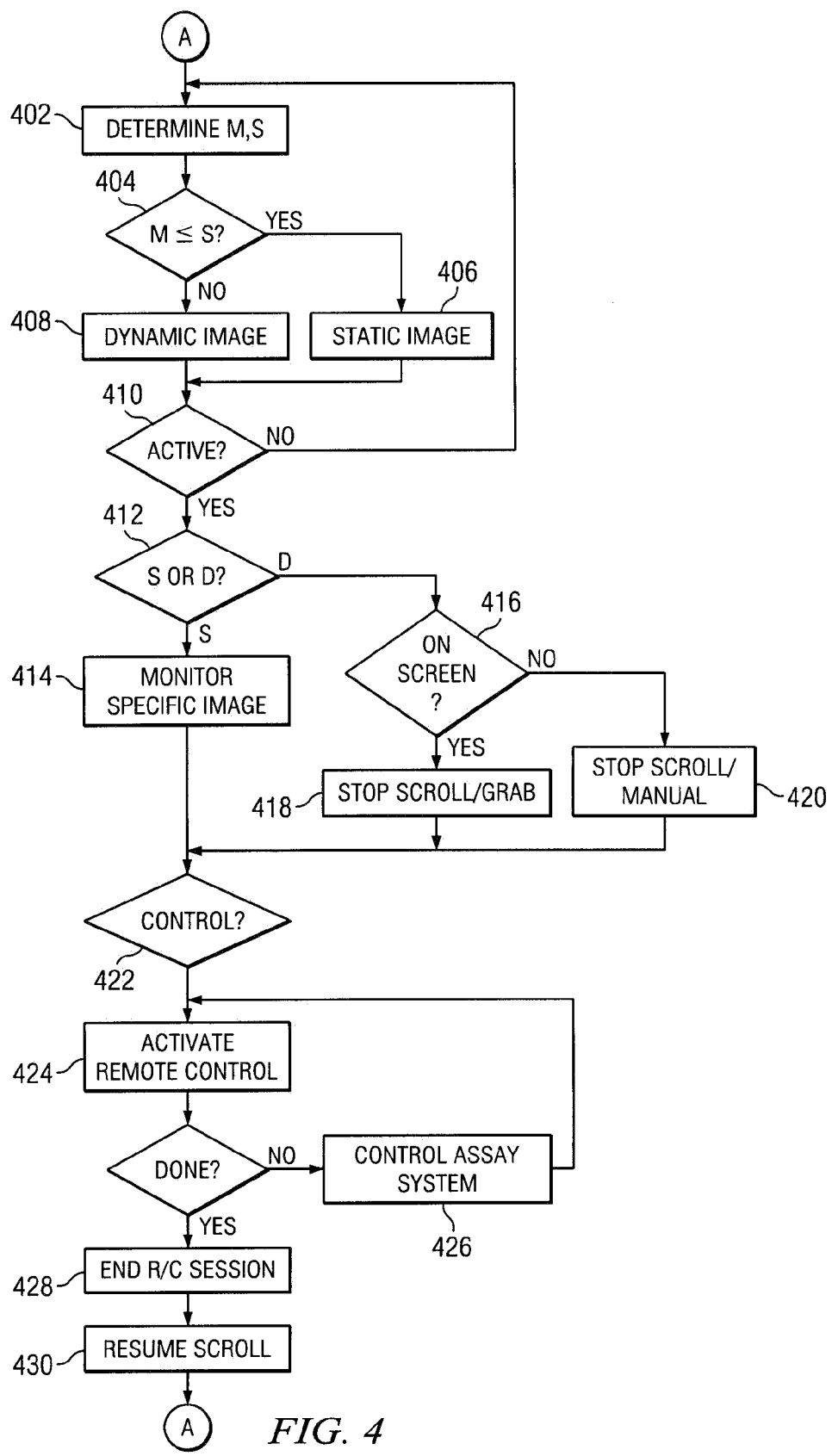
FIG. 4 shows a flow chart of a method for remotely monitoring and controlling a plurality of assay systems in accordance with the present invention.

Specific, illustrative examples embodying the appended claims are described. The examples are illustrative, for purposes of explaining the present invention by describing particular operations in reference to particular examples, thereby enabling those of ordinary skill in the relevant art to understand and practice the invention. The specific examples are not limiting but, rather, are illustrative. As will be understood by those of ordinary skill in the relevant art, upon reading this disclosure, various alternatives embodying the present invention can be readily implemented.

Features described in reference to specific embodiments are not necessarily exclusive to those specific embodiments and may be included in other embodiments.

Functional flow diagrams and their respective blocks are only illustrative logical representations of example operations and, unless otherwise specified, are not limiting as to relative time of acts or functions performed, or to a specific construction or arrangement for performing the functions.

The methods described herein may be provided as a machine-readable medium having stored, machine-readable instructions, or representations of such instructions, enabling an electronic processing machine to perform the described method. The term "machine-readable medium" includes, but is not limited to, solid-state memories, optical and magnetic disks, and any electrical or electromagnetic signal representing information.

Referring to FIG. 1, an illustrative system 10 for remotely monitoring and controlling a plurality of monitored assay systems and for practicing the method described in greater detail below will be described. Locally, the system 10 includes a plurality of monitored assay systems and associated controllers. The plurality of monitored assay systems and associated controllers can be co-located in a specific zone of the laboratory or can be distributed among several zones.

The monitored assay systems are individually labeled $12_i$, i=1 to M and collectively referenced as reference number 12. The associated controllers are individually labeled $14_i$, i=1 to N and are collectively referenced as reference number 14. Although the present invention is described as dedicating a controller 14 to each monitored assay system 12, the invention is not to be construed as being limited thereto. Those of ordinary skill in the art can appreciate that a single controller 14 can be adapted to control more than one monitored assay system 12 and/or that multiple controllers 14 can be adapted to control a single monitored assay system 12. Thus, the number of monitored assay systems M can be less than, equal to, or greater than the number of controllers N and the comparative relationship between the two can change with time.

Illustrative examples of the monitored assay systems 12 include, without limitation, commercially available units such as, the Immulite™ 2000, the Immulite™ 2500, the DPC SMS™, and the DPC T60A™, which are available from Siemens Diagnostics, Inc. Those of ordinary skill in the art can appreciate that commercially available assay systems—such as the identified examples—typically include an integrated or associated controller, which can be implemented as one or more of the controllers 14.

Controllers 14 associated or integrated with each of the monitored assay systems 12 are connected to a communication network 16, e.g., a local area network (LAN), a wide area network (WAN), the Internet, a wireless network, an Ethernet network, and the like.

Referring to FIG. 2, the controller 14 includes a network interface 206 for connecting the controller 14 to the communication network 16 and a controller interface 208 for connecting the controller 14 to its respective monitored assay system(s) 12. Those of ordinary skill in the art will appreciate that the controllers 14 can be implemented using different specific hardware units, duplicates of a common hardware unit, as discrete software modules within a single hardware unit, and other processing resources.

The controller 14 further includes a storage medium 202, a programmable processor 204, and at least one I/O device 210. The storage medium 202 retrievably stores machine-readable instructions and other data. Machine-readable instructions for the controller 14 can include assay sequences and protocols, report formats, local machine diagnostics, and, typically, an operating system. The storage medium 202 can include volatile and non-volatile memory such as, respectively, random access memory (RAM) and read-only memory (ROM), which are well-known in their various forms to those of ordinary skill in the art.

The programmable processor 204 can be implemented by a central processing unit that is arranged to execute the machine-readable instructions. A bus 212 can be provided to facilitate data communications internal to the controller 14.

Each I/O device 210 provides a user interface for communicating with the associated controller 14 as well as with any of the controllers 14 coupled to the communication network 16, with any of the monitored assay systems 12 coupled to any of the controllers 14, and/or with the remote monitoring unit(s) 18. The input portion of the I/O device(s) 210 can be implemented as a touch screen device, a control stick, an air pen, a keyboard, a keypad, a mouse, and similar GUI devices. The output portion of the I/O device(s) 210 can be implemented as a monitor display screen.

Optionally, the controller interface 208 can include means for communicating digital control data between the controller 14 and, for example, sensors and/or actuators (not shown) that are disposed at discrete locations, e.g., testing stations, within the respective monitored assay system(s) 12.

With respect to FIG. 3, the system 10 includes at least one display device that is disposed remotely from the monitored assay systems 12, i.e., a remote monitoring unit 18. The remote monitoring unit 18 is connected to the communication network 16 via a network interface 306, so as to be in communication with the controllers 14 and the multiple assay systems 12.

The remote monitoring unit 18 includes a storage medium 302, a programmable processor 304, and at least one I/O device 308. The remote monitoring unit 18 can also include a host bus 310 for internal communication between the storage medium 302, the programmable processor 304, and the at least one I/O device 308.

The storage medium 302 retrievably stores machine-readable instructions and other data. The storage medium 302 can include volatile and non-volatile memory such as, respectively, random access memory (RAM) and read-only memory (ROM), which are well-known in their various forms to those of ordinary skill in the art. Optionally, a mass storage unit 312 can be included with the remote monitoring unit 18.

The programmable processor 304 can be implemented by a central processing unit that is arranged to execute the machine-readable instructions. The I/O device 308 provides a user interface, for communicating with any of the controllers 14, with any of the monitored assay systems 12, and with the remote monitoring unit 18. The input portion of the I/O device 308 for the remote monitoring unit 18 can be implemented as a touch screen device, a control stick, an air pen, a keyboard, a keypad, a mouse, and similar GUI devices. The output portion of the I/O device(s) 308 can be implemented as at least one monitor display screen 20, e.g., a liquid crystal display (LCD), a plasma display, a cathode ray tube, and the like.

Having described the structure of a system 10 for remotely monitoring and controlling a plurality of assay systems 12, various applications and driver programs that can be executed on the system 10 will now be described. The applications and the structure involved with each application will be described in greater detail in the discussion of the method for remotely monitoring and controlling a plurality of monitored assay systems 12 below.

A first application enables the system 10 to concurrently monitor and to selectively control plural monitored assay systems 12 and their associated controllers 14 from a single, remote location. More particularly, the first application supports displaying a predetermined, fixed number of static images S on the monitor display screen 20 of the remote monitoring unit 18 as well as supports scrolling or streaming a plurality of dynamic images D on the monitor display screen 20 of the remote monitoring unit 18.

A second application enables the system 10 to update the static and dynamic images shown on the monitor display screen 20 of the remote monitoring unit 18 in real-time or pseudo-real time. Real-time imaging refers to the capability of the system 10 to record and transmit images of happenings and events at each monitored assay system 12 continuously and in real-time. Pseudo-real time imaging refers to the capability of the system 10 to detect changes in local imaging at the controller 14 level and to transmit any changes to the remote monitoring unit 18 after detection. Because there is a short lag time between detection and transmission, the images are shown in pseudo-real time. Pseudo-real time imaging can also refer to the capability of the system 10 to transmit images of happenings and events at each monitored assay system 12 at a periodic, predetermined time interval, such as a refresh feature on commercially available software and Internet Web sites.

A third application enables a user at the remote monitoring unit 18 to stop, to re-start, and to manually operate the scrolling or streaming motion of dynamic images D on the monitor display screen 20, e.g., using a mouse. More specifically, the manual scrolling feature allows users to "grab-hold" of any of the dynamic images D scrolling or streaming across the monitor display screen 20, to retard further automatic scrolling or streaming and, further, to manually advance the dynamic images D until a particular, desired dynamic image D is displayed on the monitor display screen 20, e.g., by moving the mouse from side-to-side. "Grab-hold" can be performed by pressing the left or right mouse function button and holding it in the down position. Automatic scrolling or streaming can also be re-started by releasing the left or right mouse function button from the down position.

A fourth application enables a remote user to control and communicate with a specific controller 14 and/or monitored assay system 12 from the remote monitoring unit 18. For example, the application provides some indicia at the controller 14 and at other remote monitoring units 18 to identify the user currently controlling the particular controller 14 and/or monitored assay system 12; enables the remote user to lock-out other users on other remoter monitoring units 18 from controlling the specific controller 14 and/or monitored assay system 12; and alerts the controller 14 and other remote monitoring unit 18 when the remote control has been deactivated. The remote control function can be performed with a single-click operation to avoid any confusion associated with first determining who presently may be controlling a particular controller 14 or monitored assay system 12 and, then, overriding that user's control.

A fifth application provides integrated event ("flag") management to notify remote users in real-time of a mechanical or inventory problem or potential problem associated with one of the monitored assay systems 12 and/or one of the controllers 14. For example, flag management can provide pop-up flag images and/or pop-up display windows on the monitor display screen 20 of the remote monitoring unit 18, to alert remote users of mechanical and/or inventory issues associated with specific controllers 14 and/or monitored assay system 12. User interaction, e.g., acknowledgement of the flag, with the pop-up flags and/or notices can be recorded electronically to provide actions taken and response times, e.g., for audit purposes. Additionally, the fifth application can include a flag management button, e.g., on a home screen image, that provides data on all flag events, such as time of occurrence, time of acknowledgement, actions taken, and the like. These data can be filtered using a plurality of parameters such as, for example, specific date, specific time, date range, time range, by assay test, by instrument type, by specific instrument, by criticality of flag, and so forth.

A sixth application provides inventory management for the monitored assay systems 12. More particularly, inventory management can provide an at-a-glance data display of the inventory of consumables and reagents, e.g., fill levels, inventory levels, critical levels, reagent expiration dates, and the like, for each monitored assay system 12 as well as maintenance data, e.g., calibration and re-calibration dates of the various testing devices associated with each testing station of each monitored assay system 12.

In a seventh application, priority samples currently running or in the queue to be run on the system 10 can be tracked. Such priority samples can include unlaunched stat or unlaunched routine tests whose expected completion time, i.e. turn-around time, is overdue or is soon to be past due. The priority sample data provided by the seventh application enables managers to monitor closely those assay tests that have already or are soon to violate the terms of a testing agreement with a particular client.

An eighth application provides reporting on productivity. A first productivity report can be a turn-around time (TAT) response report that shows, e.g., the number of assay tests that failed/passed TAT requirements (as a function of time), the percentage of assay tests completed as a function of time, and so forth. A second productivity report can be a throughput report that shows how the work load is distributed, e.g., by instrument type, by specific instrument, and so forth. A third productivity report can be a test count report that shows the number of assay runs for which the laboratory will be compensated over a selectively-defined period of time as a percentage of total tests run, which total also include assay runs for quality control, as verifiers, as adjustors, as replicates, as repeaters, and so forth, which may be required by protocol but for which the laboratory receives no compensation.

A ninth application provides quality assurance and quality control (QA/QC) data reporting, e.g., Levey-Jennings reporting, Levey-Jennings Multilevel reporting, instrument calibration reporting, and/or peer group reporting, for the testing stations or instruments at the testing stations of each of the monitored assay systems 12.

Having described a system and numerous applications associated with various aspects of remotely monitoring and controlling a plurality of assay systems, the interplay between the elements of the system and applications and a method for remotely monitoring and controlling a plurality of assay systems will now be described. A flowchart for the method is provided as FIG. 4. The method can be practiced on an architecture according to FIGS. 1-3.

Once the communication network 16 between the remote monitoring unit 18 and each of the controllers 14 and/or monitored assay systems 12 has been established, the processing unit 304 of the remote monitoring unit 18 continuously determines the number of assay systems M being monitored and for which image data are being transmitted to the remote monitoring unit 18 by the controllers 14 (STEP 402) and whether or not the number of monitored assay systems M is greater than the number of discrete, static images S that are displayable on the monitor display screen 20 of the remote monitoring unit 18 without scrolling or streaming the data (STEP 404).

For example, storage memory 302 and/or mass storage 312 can include retrievably stored data about parameters that define or calculate the total number of static images S that are displayable on the monitor display screen 20 as a function of the number of assay systems M currently being monitored as well as the usable screen area on the monitor display screen 20. The number of static images S is variable, depending on the user, the remote monitoring unit 18, available memory in the storage memory 302 and/or mass storage 312, and the size, capacity, and dimensions of the monitor display screen 20. Indeed, users could scale all of the images to fit on a single screen. However, the images may not be readily usable due to their small size.

Monitor display screens 20 with larger screen areas, as a rule, can provide a greater screen area to accommodate relatively more and/or relatively larger static images S than monitor display screens 20 with smaller screen areas. Much of this again depends, however, on the desired quality and detail of the static image S on the display screen 20, which is affected, for example, by the number of pixels per static image S, which can vary from display screen to display screen and from user to user. Some users may be predisposed to include a single horizontal row of static images S on a monitor display screen 20 while other users may prefer more than one horizontal row of static images S on the monitor display screen 20. Although horizontal rows of static images S are described in this disclosure, those of ordinary skill in the art can appreciate that vertical columns can be used instead.

Figure 5:
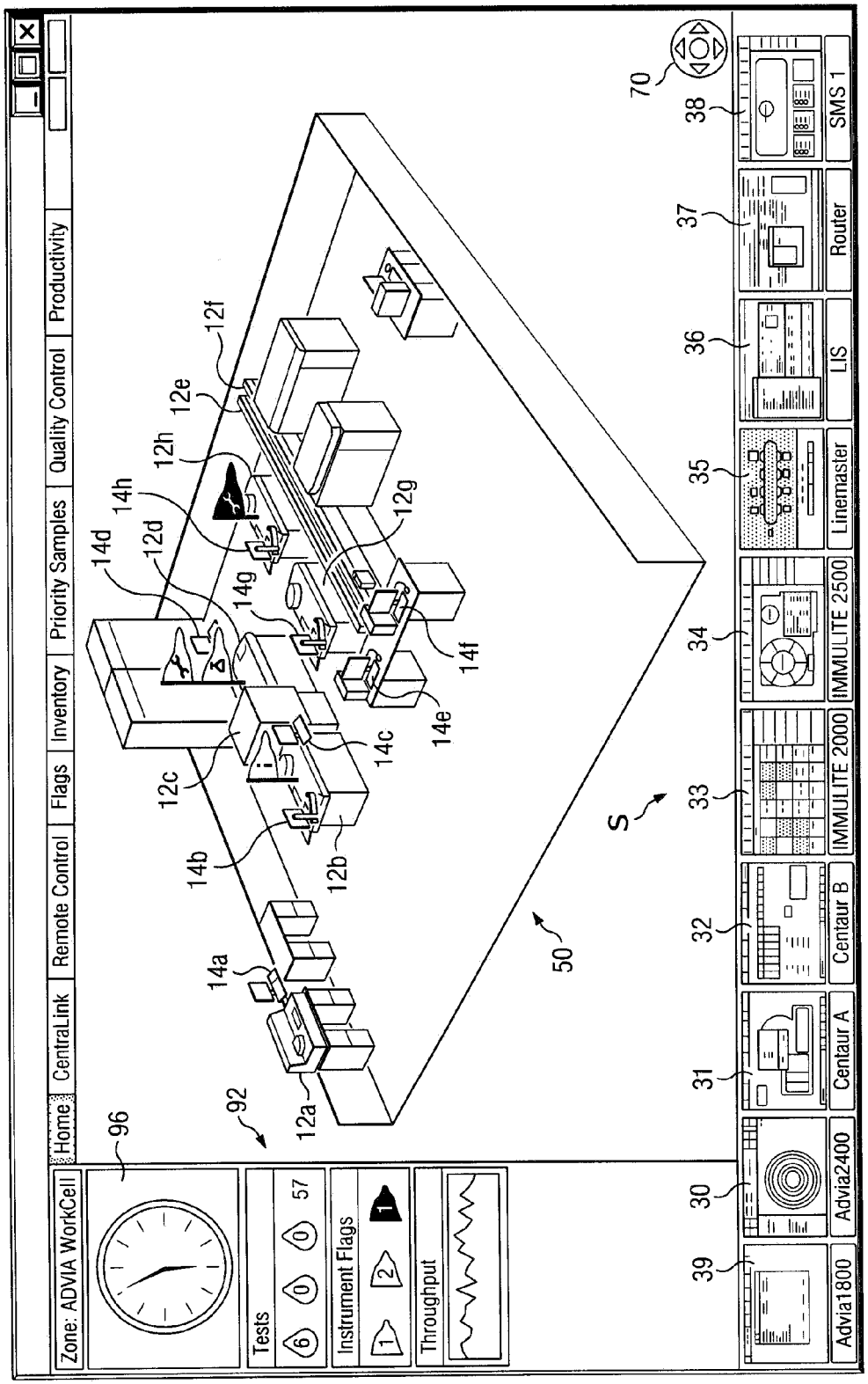
FIG. 5 shows an illustrative example of a screen image having a plurality of static images.

An illustrative example of a home page image I on a monitor display screen 20 for instances in which the number of remote assay systems M is less than or equal to the number of discrete, static images S displayable on the monitor display screen 20 (STEP 406) is shown in FIG. 5. Static, thumbnail images 30-39, which are shown horizontally and at the bottom of the image I, are not scrolled or streamed across the monitor display screen 20.

In the illustrative home page image I shown in FIG. 5, there are shown a representative, three-dimensional, isometric view 50 of the zone and lay-out of the laboratory containing monitored assay systems 12a-12h and their respective controllers 14a-14h; an event management board 92; a real-time clock 96; and thumbnail images 30-39 corresponding to each of the monitored assay systems 12a-12h. Those of ordinary skill in the art can appreciate that there are myriad of ways of presenting data and other content in conformance with the teachings of the present invention. The images I shown herein are illustrative.

Although the thumbnail images 30-39 are static, this is not to say that the thumbnail images 30-39 shown on the monitor display screen 20 do not change. Rather, the thumbnail images 30-39 do not scroll or stream across the monitor display screen 20. The processing unit 304 of the remote monitoring unit 18 and/or the processing units 204 associated with the controllers 14 are adapted to continuously transmit real-time or pseudo-real-time graphical images associated with respective monitored assay system 12 for display on the monitor display screen 20 as long as the monitored assay system 12 is operating. Each of the real-time or pseudo-real-time thumbnail images 30-39 displayed on the monitor display screen 20 of the remote monitoring unit 18 is identical to the graphical images being shown on the display device associated with the respective controller 14.

Figure 6:
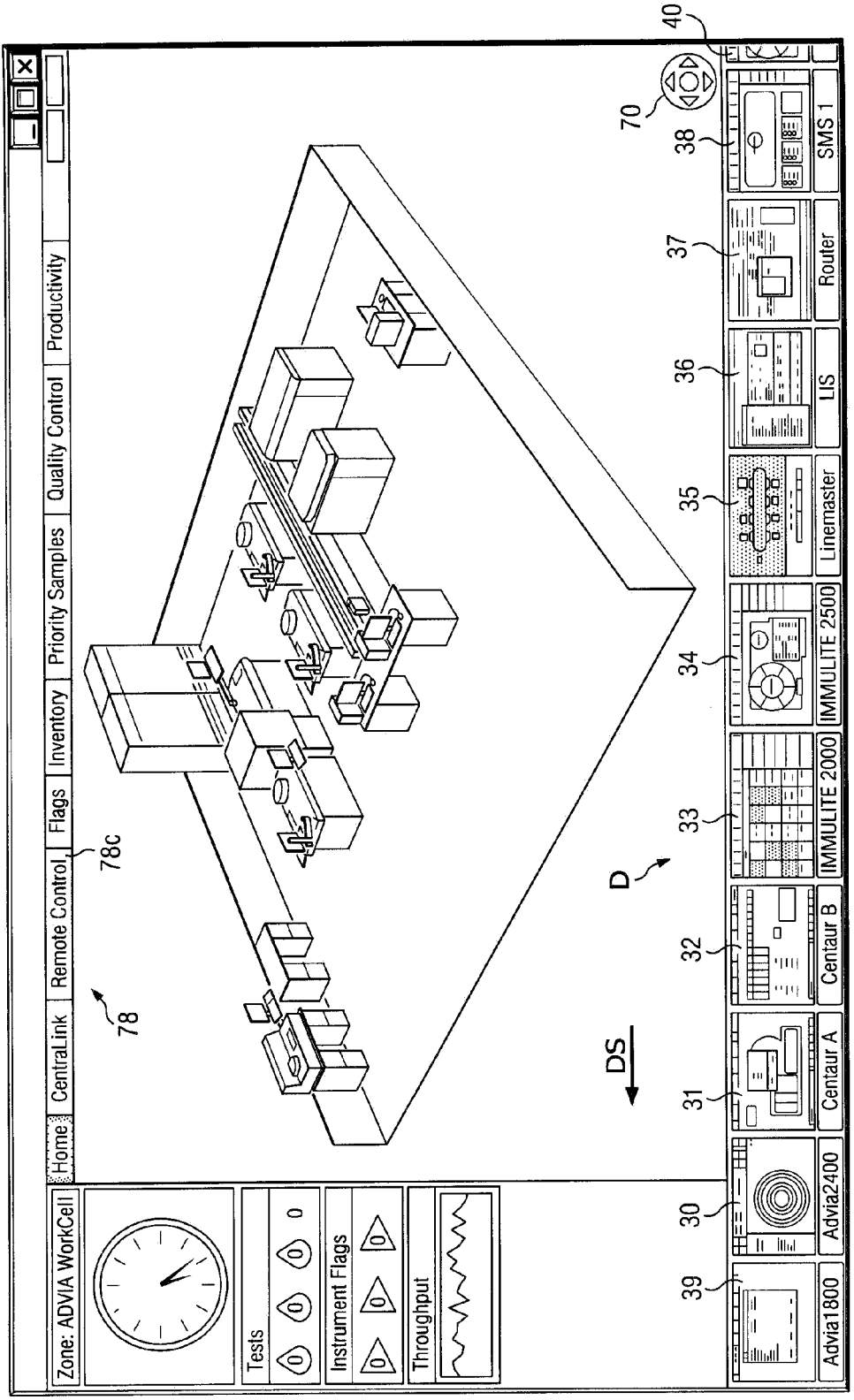
FIG. 6 shows an illustrative example of a screen image scrolling or streaming a plurality of dynamic images.

In instances in which the number of monitored assay systems M exceeds the number of displayable static images S, the images are automatically and dynamically displayed on the monitor display screen 20 of the remote monitoring unit 18 (STEP 408). Accordingly, the remote user does not have to initiate scrolling or streaming motion. Dynamic images D are shown continuously by scrolling or streaming each thumbnail image across the monitor display screen 20. For example, FIG. 6 shows a home page image I with a scrolling or streaming of images 30-40. The direction of scrolling or streaming is shown by arrow labeled DS. The order of the scrolling or streaming thumbnail images 30-40 can be arbitrary, fixed by the user or can be event-based. Because the number of monitored assay systems M exceeds the number of displayable static images S, some portion or all of at least one thumbnail image 40 is temporarily not shown.

The scrolling or streaming motion of the dynamic images D can be in a ticker-tape fashion, moving, for example, in a right-to-left direction (as shown) or in a left-to-right direction across an area such as a bottom portion or a top portion of the home page image I.

As mentioned previously, the direction of scrolling or streaming motion of the dynamic images D can also be vertical, e.g., from top-to-bottom or from bottom-to-top, on the left and/or right vertical portions of the image I on the monitor display screen 20. The rate or speed of motion of the dynamic images D can be controlled at a predetermined slow or gentle rate. Optionally, machine-executable instructions for performing step 408 can be arranged to provide user adjustment of the rate or speed of the scrolling or streaming motion.

According to the present method, whenever and while the remote monitoring unit 18 is operational and the monitor display screen 20 is displaying either static images S of the monitored assay systems 12 (STEP 406) or streaming or scrolling dynamic images D of the monitored assay systems 12 (STEP 408), the processing unit 304 continuously monitors the remote monitoring unit 18, e.g., the input portion of the I/O device 308, for indicia that a remote user desires to interface with a specific static image S or with a specific dynamic image D corresponding to a discrete monitored assay system 12 (STEP 410). Until the remote user signals or otherwise commands the processing unit 304 of the same, e.g., by logging-in, by entering a command or password, by dragging a mouse or clicking a mouse function button, and the like, the processing unit 304 of the remote monitoring unit 18 and/or the controllers 14 of the monitored assay systems 12 will continue to perform STEP 402 through STEP 408.

Once the processing unit 304 detects such indicia, and depending on whether static images S are being shown or dynamic images D are being streamed or scrolled across the monitor display screen 20 (STEP 412), the remote user will be able to interface with and, if desired, to control the controller 14 and/or the respective monitored assay system 12 that is/are associated with one of the thumbnail images (STEP 410) being displayed on the monitor display screen 20.

For example, when static images S are being shown on the monitor display screen 20, the user can interface with a specific controller 14 and/or its associated monitored assay system 12 by highlighting the respective thumbnail image using, for example, a touch-sensitive screen, a function button of a mouse, an air-pen, and the like (STEP 414). For example, if a mouse is used, the remote user can click or double-click on the associated thumbnail image using the right or left mouse function button. Alternatively, a "remote control" button 78c included in a main menu 78 on the image I can be selected, causing a data grid containing the names of each monitored assay system 12 in the zone to appear. The remote user can then highlight and click-on the name of the monitored assay system 12 of interest.

Once a desired monitored assay system 12 has been selected via its respective thumbnail image, the size of the thumbnail image 63 is enlarged automatically or, alternatively, can be enlarged, e.g., by using a zoom command or a maximize button, by using a second-click or a double-click of a left or right mouse function button, and the like. Also, as will be described in greater detail below, the remote user can opt to remotely control the controller 14 and/or monitored assay system 12 associated with the specific thumbnail image (STEP 422). It should be noted that even after a remote user has selected a desired thumbnail image, is interfacing therewith or is remotely controlling the controller 14 and/or monitored assay system 12, imaging data from the controllers 14 will be communicated to the processing unit 304 for display as thumbnail images 30-39 on the monitor display screen 20 continuously and in real-time and/or pseudo-real-time.

If, instead, dynamic images D are being scrolled or streamed across the monitor display screen 20, the remote user must first ascertain visually whether or not the desired thumbnail image is shown in the image I on the monitor display screen 20 (STEP 416). If some portion or all of the desired thumbnail image is being displayed in the image I on the monitor display screen 20, and if a mouse is used, the user can "grab-hold" of the desired thumbnail image, e.g., by depressing the right or left mouse function button and holding the function button down, which will stop the scrolling or streaming motion of the dynamic images D (STEP 418). To begin the scrolling or streaming motion of the dynamic images D again, the remote user simply releases the right or left mouse function button (STEP 430).

If only a small portion of the desired thumbnail image is shown in the image I on the monitor display screen 20 or if the desired thumbnail image is not shown at all, the remote user can manually advance the dynamic images D, for example, by dragging the mouse in the direction of the scrolling and/or streaming DS or in the reverse direction of scrolling and/or streaming (STEP 420) once the remote user has stopped the scrolling or streaming motion using the "grab-hold" function. Direction arrows 41 and 42 for manually advancing the dynamic images D are shown in "grab-hold" icon 45 in FIG. 7. Remote users have the option to manually advance the dynamic images D if the remote user does not want to wait for the desired thumbnail image to appear again.

As with static images S, once a desired monitored assay system 12 has been selected via its respective thumbnail image, the size of the thumbnail image is enlarged automatically or, alternatively, can be enlarged, e.g., by using a zoom command or a maximize button, by using a second- or a double-click of a left or right mouse function button, and the like. Also, as will be described in greater detail below, the remote user can opt to remotely control the controller 14 and/or monitored assay system 12 associated with the specific thumbnail image (STEP 422). It should be noted that even after a remote user has selected a desired thumbnail image, is interfacing therewith or is remotely controlling the controller 14 and/or monitored assay system 12, imaging data from the controllers 14 will be communicated to the processing unit 304 for display as thumbnail images 30-40 on the monitor display screen 20 continuously and in real-time and/or pseudo-real-time.

According to the fourth application associated with the present invention, after designating a specific thumbnail image to view, the remote user can opt to remotely control the controller 14 and/or the respective monitored assay system 12 associated with the specific thumbnail image (STEP 422). Recall that, when the "remote control" button 78c included in the main menu 78 of the image I is selected, a data grid containing the names of each monitored assay system 12 in the zone appears, from which the remote user can highlight and click-on the name of the monitored assay system 12 of interest.

Figure 8:
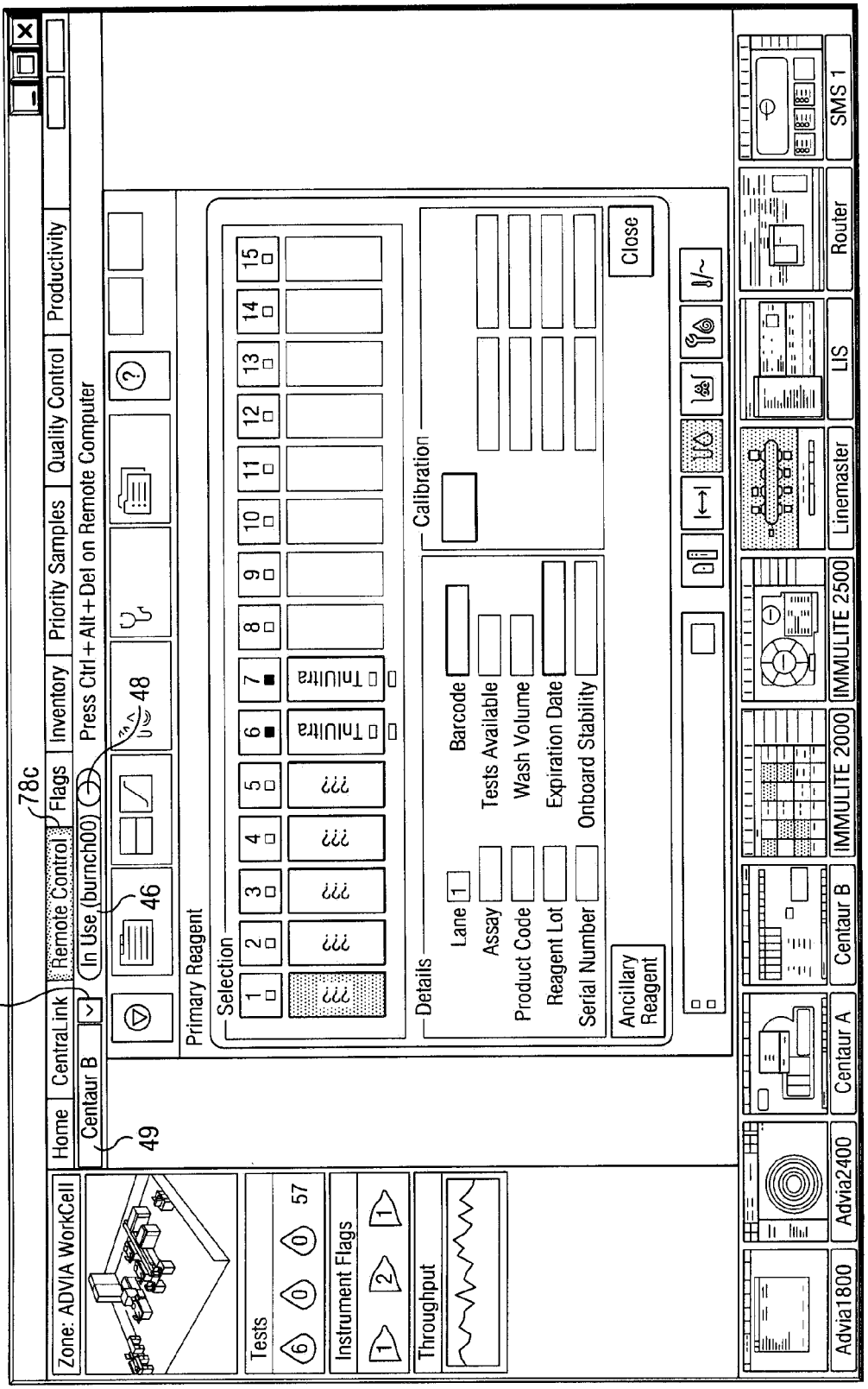
FIG. 8 shows an illustrative example of a screen image having a remote control button.

Referring to FIG. 8, an illustrative, interactive, display image L for the Centaur B assay system corresponding to thumbnail image 43 is shown. The interactive, display image L includes an instrument identification button 49 that further includes a drop-down function button 44, which, when activated, generates a data grid containing the names of all of the other monitored assay systems 12 in the zone. Users can click on any one of the monitored assay systems 12 in the drop-down data grid to jump from one assay system in the zone to another.

Shown adjacent to the identification button 49 is a virtually-slidable, remote control button 46. The remote control button 46 identifies that the controller 14 and/or respective monitored assay system 12 is "In Use" (as shown in FIG. 8) or is being remotely controlled by the remote user. The "In Use" option can connote that a remote user(s) is/are interfacing with the controller 14 and/or respective monitored assay system 12. The "Remote Control" option is an exclusive use by which other users are prevented from interacting with the controller 14 and/or respective monitored assay system 12.

The remote control button 46 embodied in FIG. 8 is virtually-movable in a like manner as the lock on the door of a lavatory on a commercial aircraft. More specifically, a remote user can "grab-hold" onto the knob 48 of the remote control button 46 and drag it horizontally, to the right or to the left. As shown in FIG. 8, by dragging the knob 48 to the left, the remote control button 46 will change from "In Use" to "Available".

Optionally, after a remote user has selected a specific thumbnail image 43 associated with a monitored assay system 12, the processing unit 304 can be adapted to automatically generate a prompt message for display on the monitor display screen 20, asking the remote user whether or not he or she would like to remotely control the controller 14 and corresponding monitored assay system 12 associated with the specific image (STEP 424). The prompt can include touch-sensitive buttons for responding to the inquiry and/or buttons that can be activated by one or more clicks using the left or right mouse function button.

Alternatively, without any prompting from the processing unit 304, the system 10 can be adapted so that a remote user can signal the processing unit 304 that he or she desires to remotely control the controller 14 and corresponding monitored assay system 12 associated with the specific thumbnail image 43. For example, the remote user can double-click the right or left mouse function button while the mouse cursor is positioned and on the thumbnail image 43 corresponding to the desired monitored assay system 12.

Once a "remote control" session has been initiated, the remote user can interact with the controller 14 and/or with the associated monitored assay system 12 corresponding to the selected thumbnail image 43 (STEP 426) until the remote user signals to the processing unit 304 and/or to the controller 14 to end the session (STEP 428).

Figure 9:
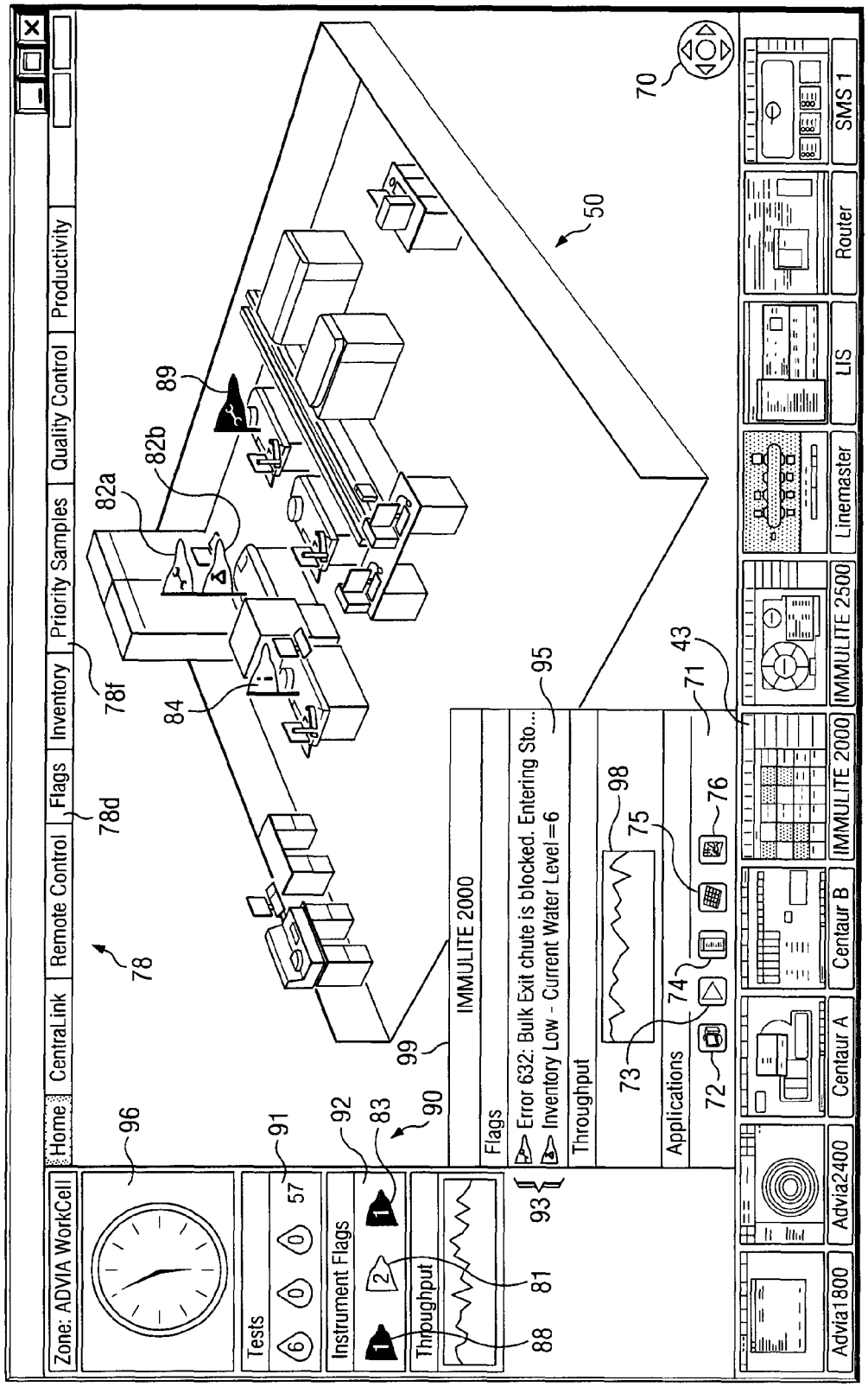
FIG. 9 shows an illustrative example of a screen image having a zone board and an instrument board.

Referring to FIG. 9, more features and applications of the present invention will be described. As mentioned previously, those of ordinary skill in the art can appreciate the myriad of ways that, for example, testing, instrument, and inventory data can be graphically displayed on a monitor display screen 20.

Each three-dimensional, isometric view 50 corresponds to a specific zone in the laboratory, in which the instruments shown in the isometric view 50 are located. The zone shown in FIG. 9 corresponds to the "ADVIA WorkCell" zone. A device 70 is included on the displayed image I to allow the remote user to rotate the direction of the perspective of the three-dimensional isometric view 50 and its pitch. Preferably, the device enables the remote user to rotate the three-dimensional isometric view 50 a full 360 degrees.

Shown vertically on the left side of the image I is a zone dashboard 90. The zone dashboard 90 graphically presents comprehensive zone data, e.g., data associated with a Laboratory Information System ("LIS") and testing statistics. The zone dashboard 90 can include a real-time clock 96 that provides the actual time at the remote monitoring unit 18. If the zone depicted in the three-dimensional isometric view of the laboratory 50 is located in a different time zone, multiple clocks 96 can be shown, representing the time at the remote monitoring unit 18 and the local time associated with the monitored assay testing system 12.

In a test section 91, for example, the number of pending (or unlaunched) tests, the number of at-risk tests, the number of overdue tests, and the number of stat tests can be provided graphically. "Stat tests" refer to those tests identified by a client, e.g., a hospital, a physician, an emergency room ("ER"), that are not routine and, therefore, require priority handling and expedited testing. "Overdue tests" refer to those test whose turn-around time ("TAT") exceeds the terms of a service agreement between the testing laboratory and a specific client. Those of ordinary skill in the art can appreciate that different tests have different TATs. The terms of service agreements, especially the TATs for identical tests, may also differ from client to client. For example, an ER may require a faster TAT than a doctor's office.

"At-risk" tests provides a summary of those tests that have yet to become overdue but which are temporally close to exceeding their TAT. Users can selectively adjust the alert time for "at-risk" tests, to provide notification any number of minutes before the test becomes overdue.

An instrument flag summary section 92 on the zone dashboard 90 provides an at-a-glance numerical summary of the number and variety of instrument flags that have been raised on discrete instruments disposed in the zone. Three varieties of instrument flags are shown in the instrument flag summary section 92 of FIG. 9: critical (red) summary flags 88, warning (yellow) summary flags 81, and information (blue) summary flags 83. The numbers shown in the summary flags 81, 83, and 88 corresponds to the number of instrument flags currently raised in the zone. According to the illustrative example in FIG. 9, there are a total of one critical flag, two warning flags, and one information flag in the "ADVIA WorkCell" zone.

"Information flags" correspond to user-created or user-defined events that can be associated with a specific instrument. Non-exclusive examples of information flags include scheduled events such as instrument calibration dates, routine maintenance dates, and the like. "Critical flags" refer to those errors that stop or hinder further testing. "Warning flags" provide advance notice of pending inventory errors as well as non-critical mechanical problems.

Instrument flags associated with a discrete instrument are generated and appear automatically as potential or existing errors, problems or shortcomings associated with a particular instrument in the zone occur. Referring to the three-dimensional, isometric view of the zone 50 in FIG. 9, instrument flags 82a, 82b, 84, and 89 are shown. The number and type of instrument flags 82a, 82b, 84, and 89 are designed to equal the numbers shown in the corresponding summary flags 81, 83, and 88. The errors, problems, or shortcomings highlighted by the information flags can include inventory errors, e.g., empty or near empty consumable levels, empty or near empty reagent levels, expired or nearly expired reagent, communication errors, and/or mechanical errors. When the error, problem or shortcoming has been rectified the instrument flag 82a, 82b, 84 or automatically disappears and the number appearing in the corresponding summary flag 81, 83, and 88 should automatically reflect the change. The opposite is also true, which is to say that until the error, problem or shortcoming has been resolved the instrument flag 82a, 82b, 84 or 89 will continue to appear.

Instrument flag management, for managing workflow and providing a means for auditing reaction time and actions taken (and by whom) to resolve errors, is one of the many applications of the present invention. For example, referring to FIG. 9, there are shown two warning flags 82a and 82b on a first instrument, one critical flag 89 on a second instrument, and an information flag 84 shown on a third instrument. Although the warning flags 82a and 82b are shown in a stacked relationship in which flag 82a is placed immediately above flag 82b, one of the warning flags could also be displayed behind the other.

When an instrument flag is generated and appears or pops-up on the monitor display screen 20, it can include or be accompanied by a visual warning to alert a remote or local user of its occurrence. If a color monitor display screen 20 is being used, the color of the instrument flags 82a, 82b, 84, and 89 can correspond to one of the three flag symbols. Furthermore, a symbol can be provided in the instrument flag to indicate whether it is an inventory issue as shown with warning flag 82b, a mechanical issue as shown with critical flag 89 and warning flag 82b or an information issue as shown with information flag 84. Although not shown, initial notification of an error associated with an instrument can include a moving or waving instrument flag and/or a blinking asterisk or other symbol (not shown) located in an upper corner of the instrument flag. The waving motion of the flag and/or the blinking asterisk features can be programmed to continue until a user has acknowledged the instrument flag. Once acknowledged, the waving motion of the flag and/or the blinking asterisk will stop.

"Acknowledging" an instrument flag 82a, 82b, 84, and 89 can be performed by clicking or double-clicking on the image of the respective instrument in the three-dimensional isometric view of the zone 50. Alternatively, a remote user can acknowledge an instrument flag by clicking on the "Flags" button 78d on the main menu 78, e.g., using a left or right mouse function button, and interacting with a drop-down data grid or pop-up message generated.

If acknowledgement does not occur within a pre-established but adjustable period of time, the processing unit 304 and/or the controllers 14 can be adapted to generate an escalation message. When an error associated with an instrument flag is escalated, a blinking exclamation point (not shown) located in an upper corner of the instrument flag can be generated and displayed. Additionally, or alternatively, a larger blinking or non-blinking exclamation point (not shown) can also be included in a pop-up message on the image I, to indicate the escalated status of the unacknowledged error message. The blinking exclamation points can continue to blink until the user has acknowledged the respective instrument flag. Once acknowledged, the exclamation points will disappear and the respective instrument flag will stop waving.

Even if acknowledged, if the error, problem or shortcoming is not resolved within a predetermined period of time, the processing unit 304 and/or the controllers 14 can be adapted to make the instrument flag 82a, 82b, 84 or 89 to begin moving or waving again and, if resolution is still not accomplished, the processing unit 304 and/or the controllers 14 can be adapted to generate another escalation message as previously described.

Clicking or double-clicking, e.g., using a left or right mouse function button, on an instrument flag in the three-dimensional isometric view of the zone 50 generates a flag detail dialog 97 corresponding to the respective flag, which is displayed on the image I. The instrument dashboard 95 corresponding to the respective instrument will be generated and displayed on the image I after an instrument from three-dimensional isometric view of the zone.

Figure 10:
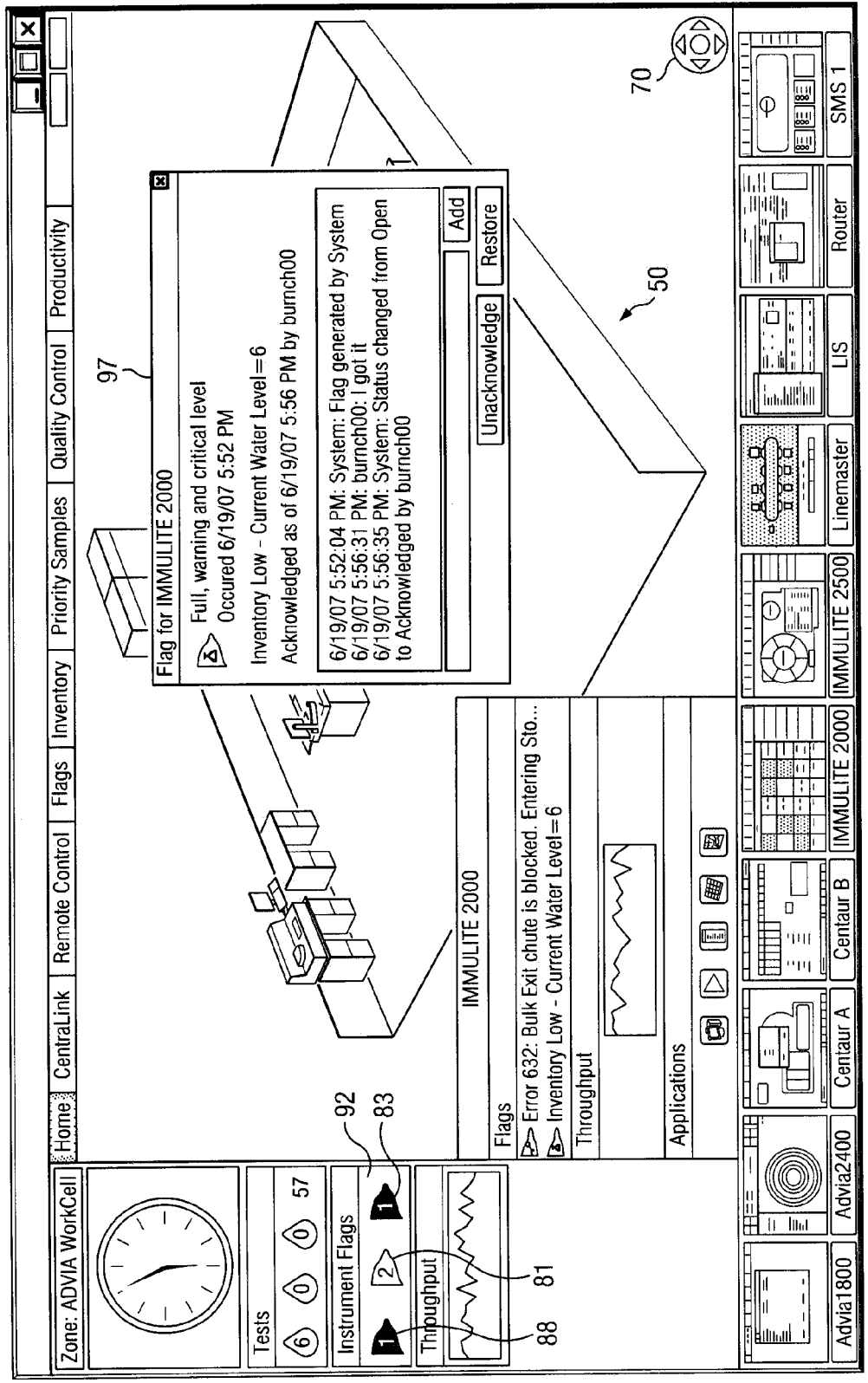
FIG. 10 shows an illustrative example of a screen image having a specific flag summary window.

The instrument dashboard 95 shown in FIG. 9 identifies the instrument type 99, e.g., the Immulite 2000, and summarizes 93 the error(s) associated with the flag(s). As further shown in FIG. 10, a data log summarizing the time of occurrence and nature of the errors or problems, date and time of acknowledgement of the errors or problems, and date and time of action(s) taken to resolve the errors or problems can be provided, e.g., using the flag detail dialog 97.

Optionally, the instrument dashboard 95 can also include a graphical representation of historical instrument throughput 98 for the instrument and an applications short-cut menu 71 for the respective instrument. The illustrative applications short-cut menu 71 shown in FIG. 9 includes a remote control short cut-button 72, a flag management short-cut button 73, inventory status short-cut button 74, a quality control short-cut button 75, and a productivity short-cut button 76. Those of ordinary skill in the art can appreciate that the short-cuts are only illustrative and additional short-cuts can also be displayed.

Figure 11:
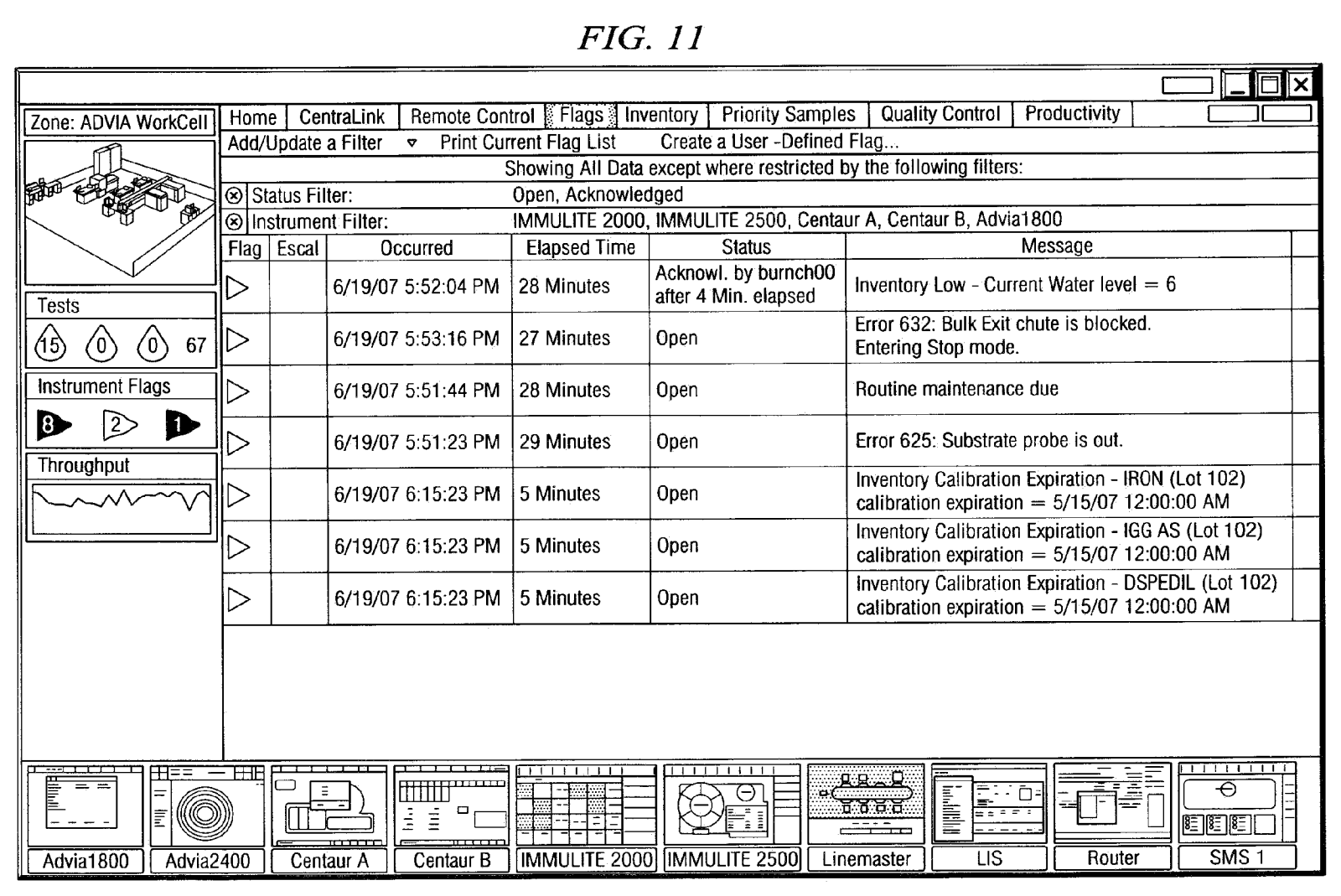

Alternatively, a user can generate a flag detail dialog 97 by clicking on the "Flags" button 78d located on the main menu 78, which will first generate a drop-down grid of flag management data (as shown in FIG. 11), listing all or some desired, filtered portion of the generated instrument flags in the displayed zone. Users can then highlight and click-on to the desired instrument flag. Referring to FIG. 11, the present invention also includes an application(s) that enables a user to filter flag management data according to or by, for example, status type, instrument type, date or time of occurrence, date or time of acknowledgement, elapsed time, acknowledged or unacknowledged (i.e., "open"), and so forth.

Figure 12A:
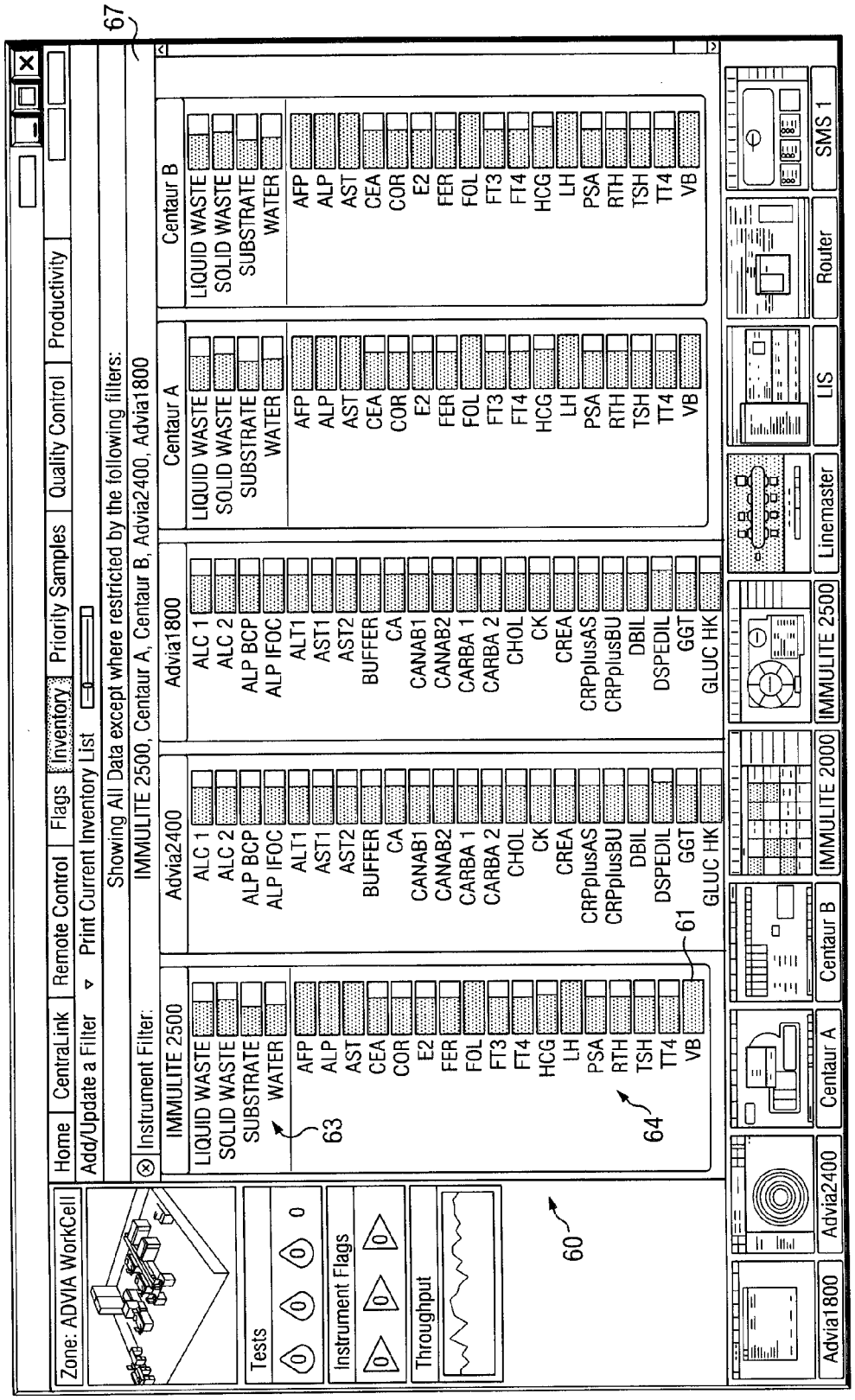
FIG. 12A shows an illustrative example of a screen image having an inventory summary window.
Figure 12B:
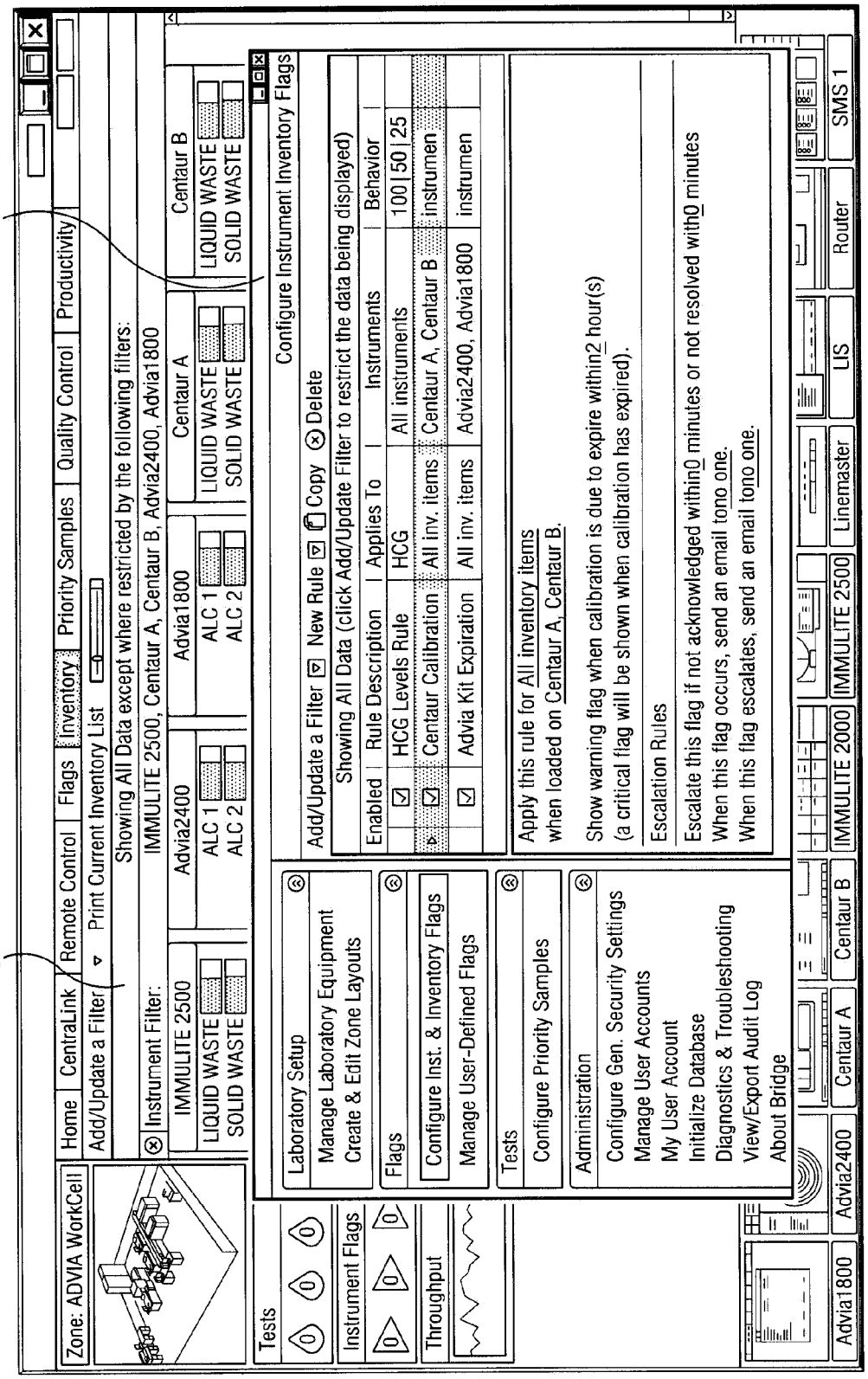

Referring to FIG. 12A and FIG. 12B, when activated, the "inventory status button" 78e and/or the inventory status short-cut button 74 and associated application(s) can generate any number of inventory management graphics 60 for any single instrument, for any combination of instruments and/or for all instruments in the zone for display on the image I. An instrument filter feature 67 enables users to see at-a-glance inventory status data for any instrument or combination of instruments in the zone.

The inventory management graphic 60, for example, can show pictorially the current fill levels 61 of all consumables 63 and specific reagents 64 associated with each discrete instrument as well as the critical or trigger levels for all consumables 63 and specific reagents 64 associated with each discrete instrument. Critical or trigger levels refer to an inventory level at which a warning or critical flag is generated. Critical or trigger levels can be selectively established by the user using an interactive application.

Although not shown in FIG. 12A or FIG. 12B, "flagged" inventory items, which is to say inventory items for which one or more warning or critical flags has/have been generated, in the inventory management graphic 60 can bubble to the top of the graphic for display above data associated with the consumables 63. More detailed information for each consumable 63 or reagent 64; for establishing critical or trigger levels; and/or for causing instrument flag escalation can be generated and displayed in a pop-up window 66, e.g., by running the mouse cursor over the respective consumable 63 or reagent 64.

Figure 13:
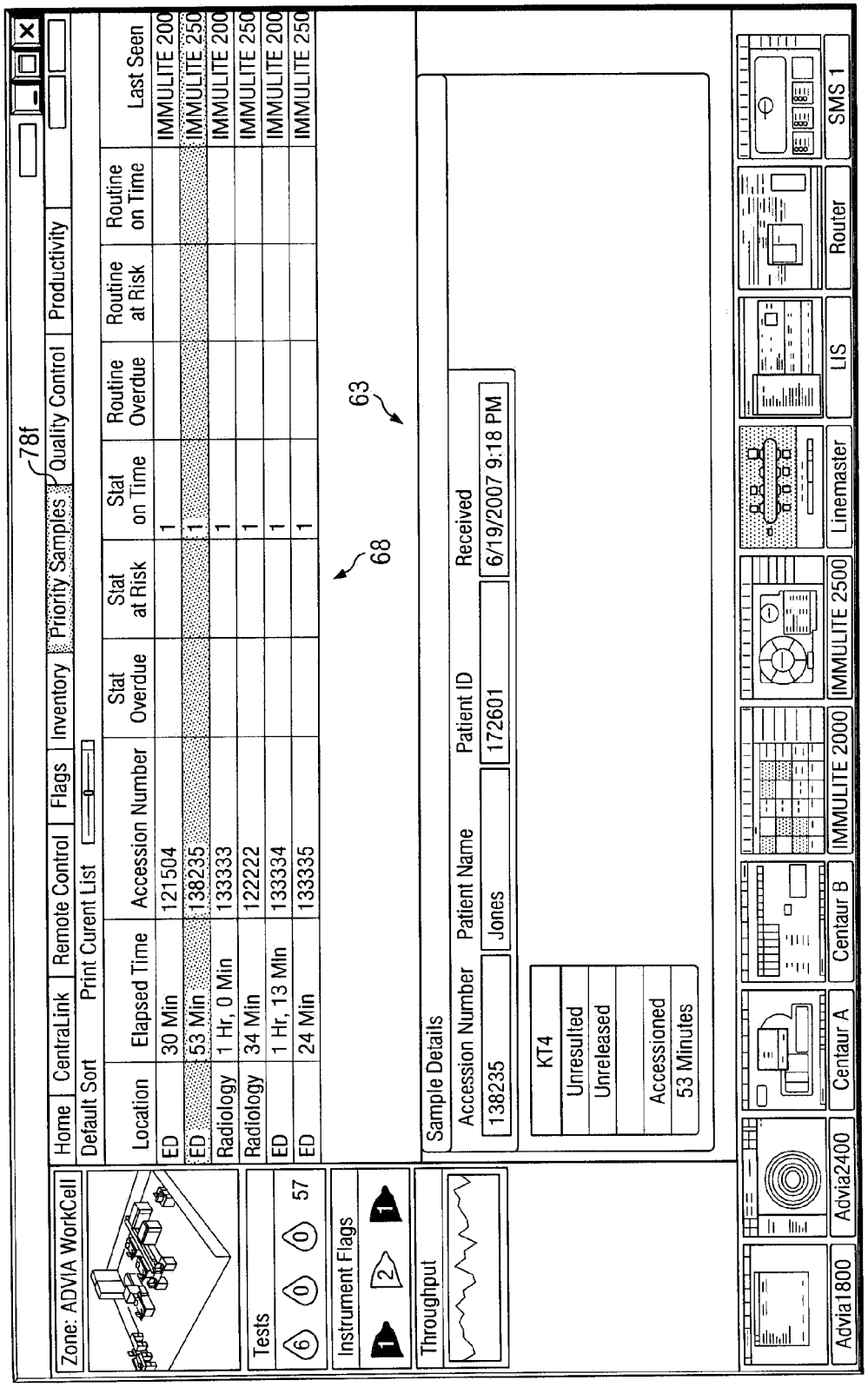
FIG. 13 shows an illustrative example of a screen image having a priority sample and sample detail windows.

The "priority sample button" 78f and associated application(s) enable users to view, sort, manipulate, and/or catalog, for example, queue data, testing data, and the like. By clicking on a "Priority Sample" button 78f on the main menu 78, e.g., using a left or right mouse function button, a pop-up window display 68 of priority tests that require action can be generated. An illustrative example of a pop-up priority test window display 68 is shown in FIG. 13. The pop-up window display 68 provides data in a tabular format. Data can include, for example, the client or point of origination of the sample, the elapsed time since sampling and/or since delivery to the laboratory, the test type(s), the assay testing instrument, the accession number, the patient's name and/or identification number, the attending physician's name, the time past due or time remaining before overdue, and the like for each of the unlaunched stat tests, the unlaunched, overdue routine tests, and any at-risk tests. Additional data, e.g., sample details 63, pertaining to a specific sample, patient, test, etc. can also be provided in a window format.

Figure 14:
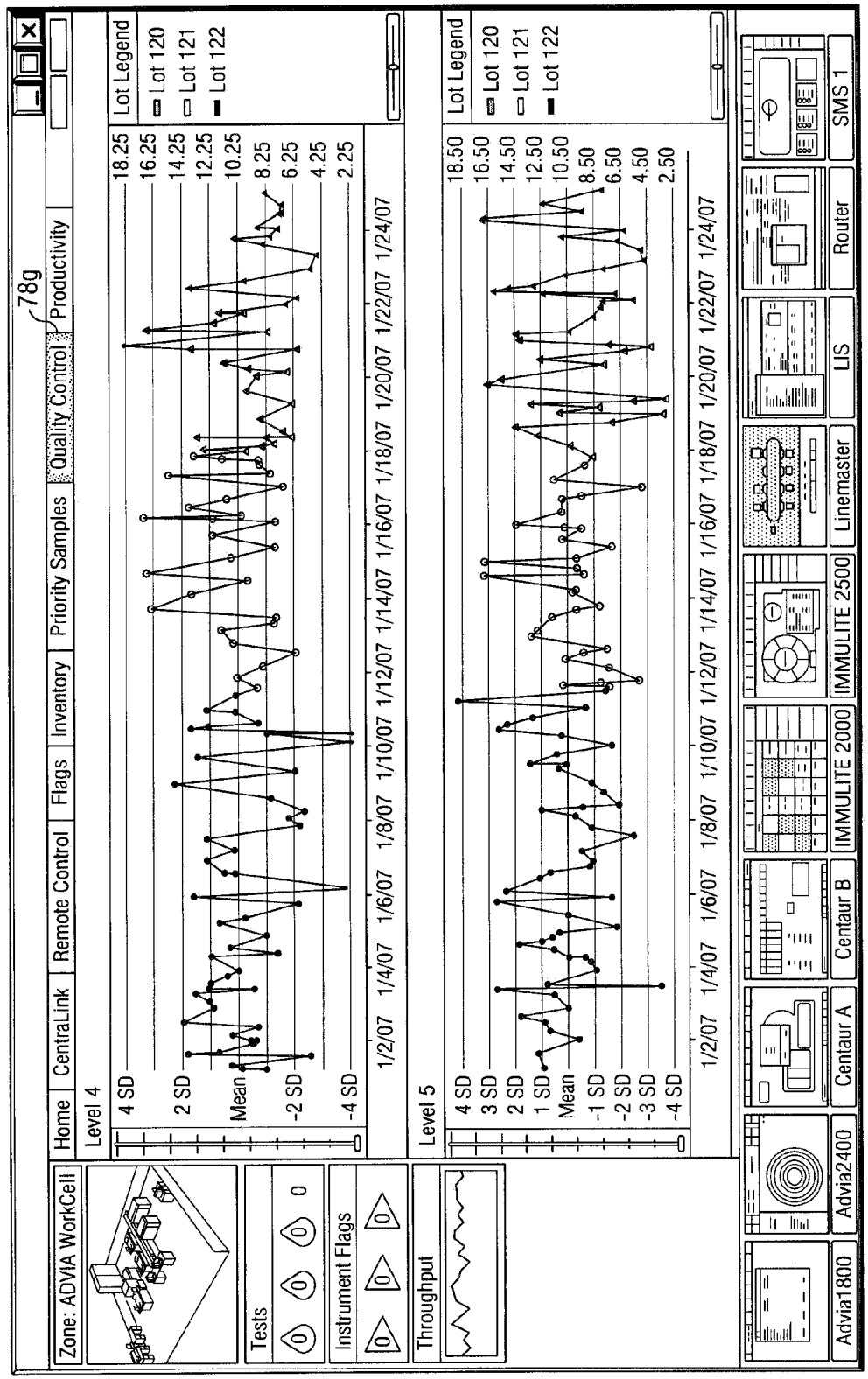
FIG. 14 shows an illustrative example of a screen image having quality control windows.

The "quality control button" 78g and/or the quality control short-cut button 75 and associated application(s) enable users to produce quality control reports such has Levey-Jennings reports, Levey-Jennings Multilevel reports, Calibration reports, Peer Group reports, and the like. FIG. 14 provides illustrative displays of quality control data.

Figure 15A:
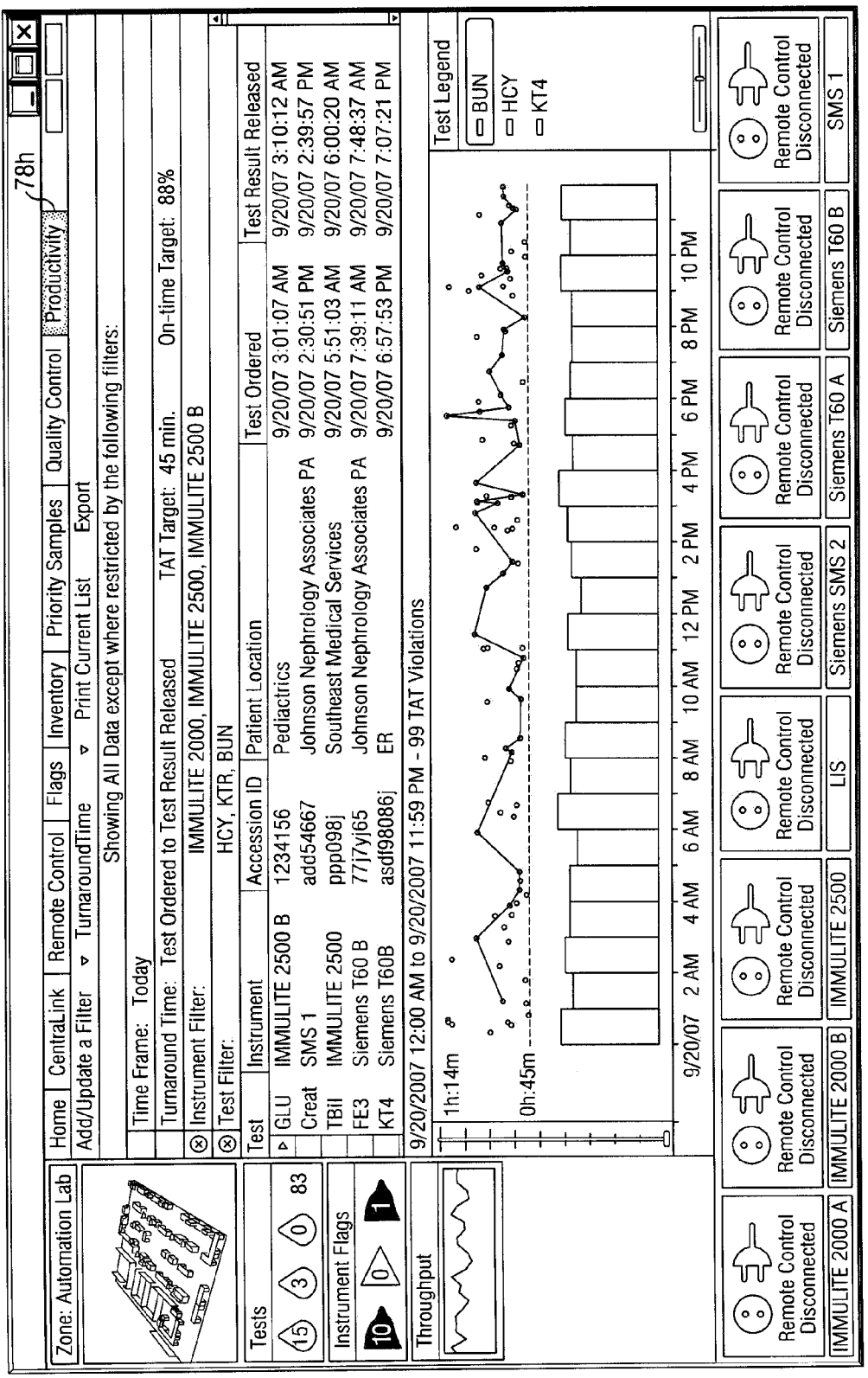
FIG. 15A-15D show illustrative examples of screen images having different displays of productivity data.

The "productivity button" 78h and/or productivity short-cut button 76 and associated application(s) enable users to produce productivity reports beyond what is provided in the graphical representation of historical instrument throughput 98 in the instrument dashboard 95. For example, FIG. 15A shows an exemplary first productivity report encompassing three test types (HCY, KT4 and BUN) that are run on three assay testing devices (IMMULITE 2000, IMMULITE 2500, and IMMULITE 2500B) based on a threshold TAT of 45 minutes. Graphical data are provided using point data (to show those data that have exceeded the threshold TAT) over specified periods of time and bar data (to show the percentage of tests that met the threshold TAT) over the same specified periods of time. Accordingly, at-a-glance, a remote user can ascertain that 99 HCY, KT4 and BUN tests run on the designated assay testing devices violated TAT goals and that 88 percent of all of the HCY, KT4 and BUN tests run on the designated assay testing devices satisfied TAT goals.

Figure 15B:
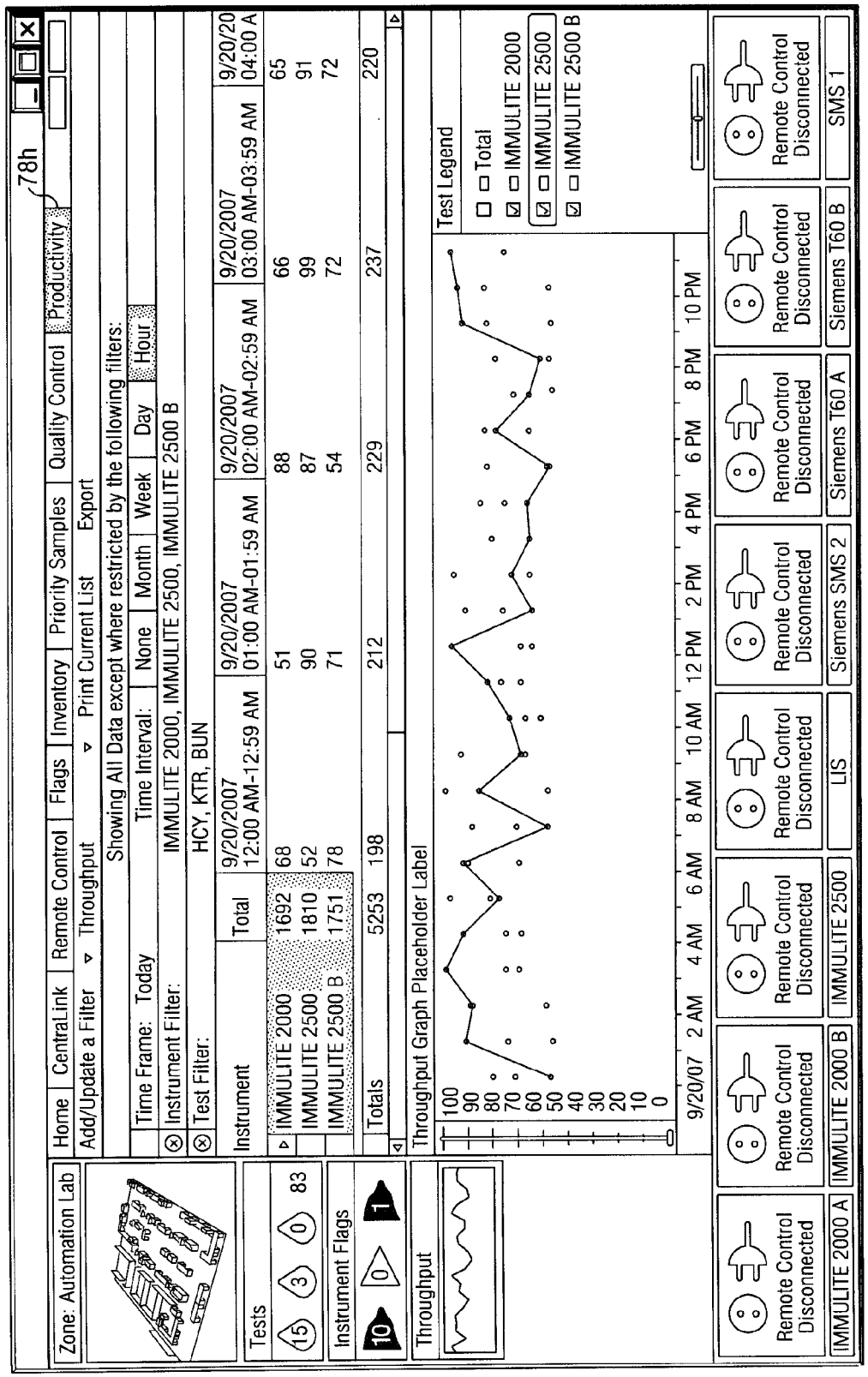

In a second productivity report, these data can be used to show how the work load is distributed, e.g., by instrument type, by specific instrument, and so forth. As shown in FIG. 15B, for the same three assay testing devices (IMMULITE 2000, IMMULITE 2500, and IMMULITE 2500B) and the same three test types (HCY, KT4 and BUN), one can see at-a-glance how many of the three tests were performed on each of the three assay testing devices with time. These data can be used to better allocate and balance the number tests between all of the instruments that can perform the desired test type.

Figure 15C:
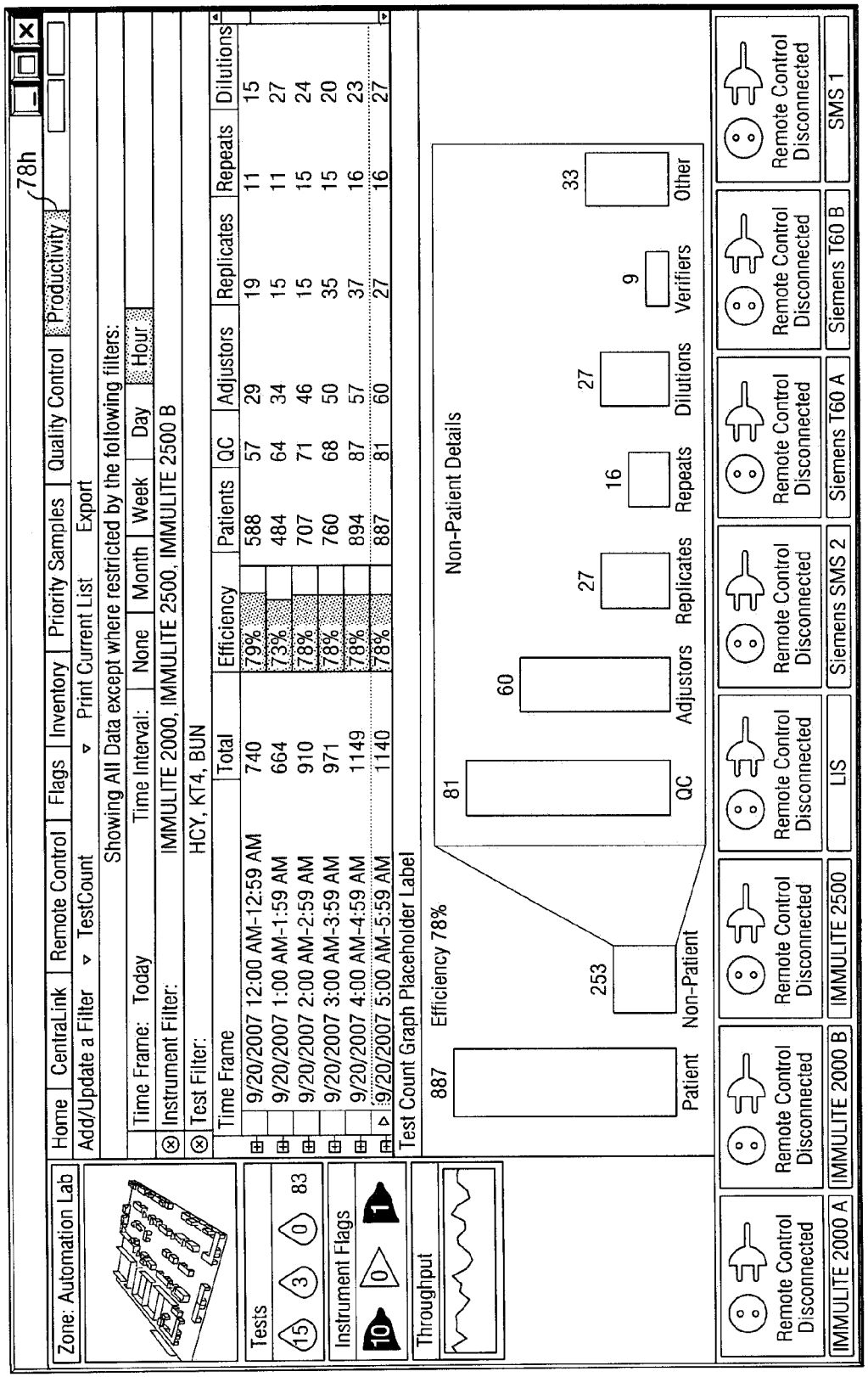

In a third productivity report, data can be used to show the number of assay runs for which the laboratory will be compensated over a selectively-defined period of time as a percentage of total tests run. As shown in FIG. 15C, for the same three assay testing devices (IMMULITE 2000, IMMULITE 2500, and IMMULITE 2500B) and the same three test types (HCY, KT4 and BUN), one can see at-a-glance the number of patient (compensated) versus non-patient (uncompensated) tests which were run during the specified period of time and the total efficiency (78%). The number of non-patient tests can be further broken down to show the number of runs for quality control, as verifiers, as adjustors, as replicates, as repeaters, as dilutions, and other tests that may be required by protocol but for which the laboratory receives no compensation.

Figure 15D:
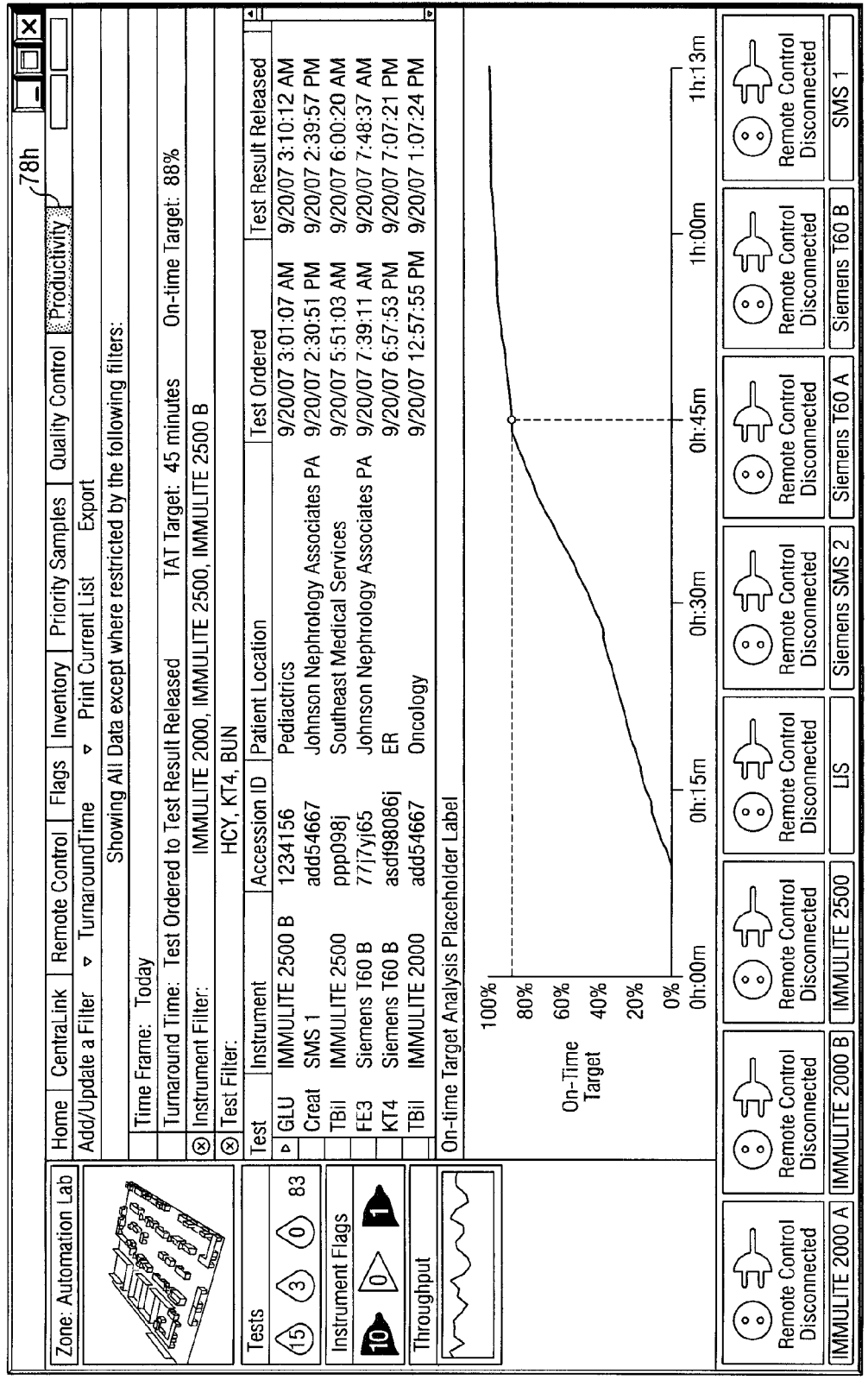

In a fourth productivity report, data can be used to show the testing time distribution and percentage of on-time tests. Referring to FIG. 15D, for the same three assay testing devices (IMMULITE 2000, IMMULITE 2500, and IMMULITE 2500B) and the same three test types (HCY, KT4 and BUN), one can see at-a-glance that 88% of all of the three tests on the three instruments passed a 45 minute TAT goal. Furthermore, one also sees at-a-glance, the marginal return in percent on-time if the TAT is increased to one hour.

While certain embodiments and features of the invention have been illustrated and described herein, many modifications, substitutions, changes, and equivalents will occur to those of ordinary skill in the art. For example, although the present invention has been described for application in connection with monitoring and controlling assay testing systems in discrete zones of a laboratory, the teachings of the present invention can be applied broadly to a variety of specific systems that are not necessarily in a laboratory. It is therefore to be understood that the appended claims are intended to cover all such modifications and changes as fall within the spirit of the invention.

What is claimed is:

1. A computer implemented method for monitoring, at a remote monitoring unit having an associated processing unit and a display, a plurality of devices that each include a processing system that is adapted to generate a display image representing a status of the associated device, the method comprising:

receiving, by the remote monitoring unit, from one or more of the plurality of devices over a computer network, data corresponding to one or more images, each image being indicative of an operational status of the device from which the image was received;

determining, via the processing unit, a number of images in the received one or more images and whether the number of images is greater than a predetermined threshold number of images;

in the event the determining step indicates that the number of images is not greater than the predetermined threshold number of images, concurrently displaying in real-time or pseudo-real-time each one of the one or more images on the display associated with the remote monitoring unit;

in the event the determining step indicates that the number of images is two or more images and greater than the threshold number of images, sequentially displaying subsets of the images on the display associated with the remote monitoring unit such that the images in each subset are displayed concurrently and in real-time or pseudo-real-time for a predetermined time interval and each image of the two or more images is at least periodically visible in at least one of the subsets; and displaying a priority status with an image displayed on the display associated with the remote monitoring unit, the priority status being related to an item that is identified for a priority of processing in the device from which data corresponding to the respective image was received.

2. The method of claim 1, further comprising receiving a first user-entered command and, in response to the first user-entered command, stopping sequential display of the subsets such that a subset displayed on the display of the remote monitoring unit remains displayed on the display.

3. The method of claim 2, further comprising, following receipt of the first user-entered command, receiving a second user-entered command and, in response to receipt of the second-user entered command, restarting sequential displaying of the subsets in the second display mode.

4. The method of claim 1, further comprising initiating a user-requested remote, over-ride session via the remote monitoring unit in connection with one of the devices associated with a selected one of the one or more images.

5. A system for remotely monitoring a status of a plurality of devices that are each operative to generate and transmit at least one image, the system comprising:
 a monitor unit, communicably coupled to each one of the plurality of devices via a computer network, the monitor unit including an associated display, a user interface, and a processing unit, the processing unit configured to receive data corresponding to one or more images from the plurality of devices and display the one or more images on the display associated with the remote monitoring unit in real-time or pseudo-real-time, each image being indicative of an operational status of the device from which the image was received, the processing unit being operative to:
 determine a number of images in the one or more images and whether the number of images in the one or more images represents more than a predetermined threshold number of images;
 in the event it is determined that the one or more images is not greater than the threshold number of images, concurrently display each image of the one or more images on the display device of the monitor unit;
 in the event it is determined that the one or more images is two or more images and that the number of images is greater than the threshold number of images, display the two or more images sequentially as subsets of images such that one or more images in each subset are displayed concurrently for a predetermined time interval on the display device of the monitor unit with each image of the two or more images at least periodically visible in at least one of the subsets; and
 display a priority status with an image displayed on the display associated with the remote monitoring unit, the priority status being related to an item that is identified for a priority of processing in the device from which data corresponding to the respective image was received.

6. The system according to claim 5, wherein the processing unit is operative, in response to a user input to control display of the two or more images displayed in at least one of the subsets of images.

7. The system according to claim 6, wherein the processing unit is operative to stop the sequential display of subsets of images in response to the user input.

8. The system according to claim 5, wherein the processing unit is further operative to initiate a remote, over-ride session with a selected one of the plurality of devices in accordance with a user input indicating a selection of an image associated with the selected device.

9. The method according to claim 1, further comprising, in response to a user input, blocking inputs from another remote monitoring unit to a selected one of the plurality of devices associated with a selected display image of the one or more images.

10. The method according to claim 4, further comprising providing a status indication of the over-ride session to the one of the devices that is associated with the selected one of the one or more images.

11. The method according to claim 1, further comprising concurrently displaying all of the one or more images on the display in real-time or pseudo real-time and concurrently displaying the images of each subset on the display, in real-time or pseudo-real-time.

12. The method according to claim 1, further comprising displaying a flag with each image displayed on the display associated with the remote monitoring unit to indicate a status of an item related to operation of the device from which the respective image was received.

13. The system according to claim 5, wherein the processing unit is operative to display a flag with each image displayed on the display associated with the monitor unit to indicate a status of an item related to operation of the device from which the data corresponding to the respective image was received.

14. The system according to claim 5, wherein the processing unit is operative to display a priority status with an image displayed on the display associated with the monitor unit related to an item that is identified for priority processing in the device from which the respective image was received.

15. A computer program product embodied on a non-transient computer readable medium, the computer program product comprising software code stored on the computer readable medium and executable on a processing unit associated with a monitoring unit, the software code being operable, upon execution by the processing unit to:
 receive over a computer network, by the monitoring unit, from one or more of a plurality of devices remote from the monitoring unit, data corresponding to one or more images indicative of an operational status of the device from which the respective image was received;
 determine, via the processing unit, a number of images in the received one or more images and whether the number of images is greater than a predetermined threshold number of images;
 in the event the processing unit determines that the number of images is not greater than the predetermined threshold number of images, concurrently display in real-time or pseudo-real-time each one of the one or more images on the display associated with the monitoring unit;
 in the event the processing unit determines that the number of images is two or more images and that the number of images is greater than the threshold number of images, sequentially displaying subsets of the images on the display associated with the monitoring unit such that the images in each subset are displayed concurrently and in real-time or pseudo-real -time for a predetermined time interval and each image of the two or more images is at least periodically visible in at least one of the subset; and
 display a priority status with an image displayed on the display associated with the remote monitoring unit, the priority status being related to an item that is identified for a priority of processing in the device from which data corresponding to the respective image was received.

16. The method of claim 1 further comprising:
 stopping the sequential displaying of the subsets on the display of the remote monitoring unit in response to a second user input at the remote monitoring unit; and
 manually advancing from a display of one subset to a display of another subset in response to a further user input to the remote monitoring unit.

17. A computer implemented method for monitoring, at a remote monitoring unit having an associated processing unit and a display, a plurality of devices, each of which include a processing system that is adapted to generate a display image representing a status of the associated device, the method comprising:

receiving over a computer network, by the remote monitoring unit, from one or more of the plurality of devices, data corresponding to one or more images indicative of an operational status of the device from which the respective image was received;

determining, via the processing unit, a number of images in the received one or more images and whether the number of images is greater than a predetermined threshold number of images;

in the event the determining step indicates that the number of images is not greater than the predetermined threshold number of images, concurrently displaying in real-time or pseudo-real-time each one of the one or more images on the display associated with the remote monitoring unit;

in the event the determining step indicates that the number of images is two or more images and the number of images is greater than the threshold number of images, sequentially displaying in real-time or pseudo-real-time the two or more images on the display associated with the remote monitoring unit by scrolling the two or more images across the display such that each image of the two or more images is at least periodically visible during the scrolling of the two or more images; and displaying a priority status with an image displayed on the display associated with the remote monitoring unit, the priority status being related to an item that is identified for a priority of processing in the device from which data corresponding to the respective image was received.

18. The method of claim 17 further including the step of displaying a plurality of the two or more images on the display concurrently during the scrolling of the images across the display.

* * * * *